United States Patent
Ohyu et al.

(10) Patent No.: US 9,734,578 B2
(45) Date of Patent: Aug. 15, 2017

(54) MEDICAL IMAGE ANALYZER

(71) Applicant: Toshiba Medical Systems Corporation, Otawara-shi (JP)

(72) Inventors: Shigeharu Ohyu, Yaita (JP); Yasuko Fujisawa, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 90 days.

(21) Appl. No.: 14/940,260

(22) Filed: Nov. 13, 2015

(65) Prior Publication Data

US 2016/0140712 A1 May 19, 2016

Related U.S. Application Data

(63) Continuation of application No. PCT/JP2014/062745, filed on May 13, 2014.

(30) Foreign Application Priority Data

May 13, 2013 (JP) .................................. 2013-101689
May 13, 2013 (JP) .................................. 2013-101690

(51) Int. Cl.
G06T 7/00 (2017.01)
A61B 6/00 (2006.01)
A61B 5/055 (2006.01)

(52) U.S. Cl.
CPC ............ *G06T 7/0016* (2013.01); *A61B 6/481* (2013.01); *A61B 6/486* (2013.01); *A61B 6/507* (2013.01);
(Continued)

(58) Field of Classification Search
CPC combination set(s) only.
See application file for complete search history.

(56) References Cited

U.S. PATENT DOCUMENTS 7,369,691 B2 * 5/2008 Kondo ..................... G06T 15/08
382/128
7,774,041 B2 * 8/2010 Nambu .................. A61B 6/463
378/19

(Continued)

FOREIGN PATENT DOCUMENTS

JP 2003-210456 7/2003
JP 2008-43736 2/2008

(Continued)

OTHER PUBLICATIONS

English translation of the International Search Report issued Jul. 22, 2014 in PCT/JP2014/062745, filed on May 13, 2014.

(Continued)

*Primary Examiner* — Anand Bhatnagar
(74) *Attorney, Agent, or Firm* — Oblon, McClelland, Maier & Neustadt, L.L.P.

(57) ABSTRACT

According to one embodiment, a medical image analyzer includes a retriever, a first artery transition information unit, a vessel pixel selector, a blood vessel transition information unit, an image association unit, and a second artery transition information unit. The retriever retrieves a plurality of time-series images. The first artery transition information unit obtains first artery transition information. The vessel pixel selector selects vessel pixels. The blood vessel transition information unit obtains blood vessel transition information. The image association unit obtains a correspondence relationship between one and another of the time-series images. The second artery transition information unit obtains second artery transition information based on time information, the first artery transition information, and the blood vessel transition information, and the correspondence relationship.

13 Claims, 13 Drawing Sheets

(52) U.S. Cl.
CPC ......... *A61B 5/0555* (2013.01); *A61B 2576/00* (2013.01); *G06T 2207/10081* (2013.01); *G06T 2207/10088* (2013.01); *G06T 2207/20224* (2013.01); *G06T 2207/30104* (2013.01)

(56) References Cited

U.S. PATENT DOCUMENTS

| | | | |
|---|---|---|---|
| 8,126,227 B2* | 2/2012 | Fujisawa | A61B 6/032 128/922 |
| 8,315,449 B2* | 11/2012 | Kemper | G06K 9/6223 382/128 |
| 8,792,616 B2* | 7/2014 | Tanaka | A61B 6/0457 378/20 |
| 2003/0097076 A1* | 5/2003 | Nambu | A61B 6/463 600/504 |
| 2004/0002646 A1 | 1/2004 | Oesingmann | |
| 2007/0263915 A1* | 11/2007 | Mashiach | G06K 9/342 382/130 |
| 2008/0019580 A1 | 1/2008 | Ohyu et al. | |
| 2008/0075344 A1* | 3/2008 | Nambu | A61B 6/463 382/131 |
| 2010/0067767 A1* | 3/2010 | Arakita | A61B 6/507 382/131 |
| 2011/0130668 A1* | 6/2011 | Ohyu | A61B 5/0263 600/504 |
| 2011/0206183 A1* | 8/2011 | Tanaka | A61B 6/0457 378/62 |
| 2013/0225958 A1* | 8/2013 | Ichihara | A61B 6/481 600/363 |
| 2013/0243301 A1 | 9/2013 | Sakaguchi et al. | |
| 2014/0003687 A1* | 1/2014 | Jou | A61B 6/481 382/130 |
| 2014/0233814 A1* | 8/2014 | Ikeda | A61B 6/507 382/128 |
| 2015/0150526 A1* | 6/2015 | Ohishi | A61B 6/463 378/62 |

FOREIGN PATENT DOCUMENTS

| | | |
|---|---|---|
| JP | 2010-68958 | 4/2010 |
| JP | 4454960 | 4/2010 |
| JP | 2011-172644 | 9/2011 |
| JP | 2012-90883 | 5/2012 |

OTHER PUBLICATIONS

Hidenori Shikata, et al., "An Algorithm for Localizing Branch Points of Pulmonary Vessels for Non-Rigid Registration of the Lungs" The Institute of Electronics Information and Communication Engineers (IEICE) Trans., vol. J85-D-II, No. 10, Oct. 2002, pp. 1613-1623 (with English Abstract and partial English translation).

\* cited by examiner

MEDICAL IMAGE ANALYZER

CROSS-REFERENCE TO RELATED APPLICATION

This application is based upon and claims the benefit of priority from Japanese Patent Application Nos. 2013-101689, filed 13 May 2013 and 2013-101690, filed 13 May 2013; the entire contents of which are incorporated herein by reference.

FIELD

Embodiments described herein relate generally to a medical image analyzer.

BACKGROUND

A medical image capturing apparatus such as an X-ray computed tomography (CT) apparatus, a magnetic resonance imaging (MRI) apparatus or the like is used to capture time-series images of a subject to which a contrast agent has been administered to obtain information about the blood flow dynamics of tissue by analyzing the images. This is called perfusion analysis, which uses the fact that the concentration of the contrast agent in the tissue can be obtained from the value of a pixel corresponding to the tissue in the image.

For example, deconvolution method is used as a common perfusion analysis method. In the deconvolution method, using a time density curve in an artery in the immediate vicinity of the tissue as an input function, the deconvolution (inverse convolution integration) of the time density curve of the tissue is performed to obtain the impulse response function of the tissue. Then, from the impulse response function, the blood-flow volume, average transit time, blood volume, and the like representing the blood flow dynamics of the tissue are calculated. Besides, maximum slope method may be used as another perfusion analysis method. In the maximum slope method, the blood-flow volume is calculated through the division of the maximum slope of the rising portion of transition information in the time density curve of the tissue and the maximum value of the time density curve of the artery. Note that the time density curve is a curve representing the transition of the concentration of the contrast agent (density of contrast) measured in a graph. The term "transition information" as used herein refers to information that indicates the transition of the concentration of the contrast agent.

The time-series images of the subject having been administered a contrast agent are typically captured by securing the position of the bed of the apparatus and repeatedly capturing (volume scanning) the image of a predetermined area at regular intervals. The time-series images include a plurality of still images. For example, when the medical image capturing apparatus performs volume scan 60 times at intervals of 1 second, time-series images of one minute consisting of 60 frames are obtained for the area. The medical image analyzer performs the perfusion analysis of the time-series images obtained in this way.

In capturing a large tissue such as lung, brain, liver, or the like, the image of an area including the whole tissue may not sometimes be captured. Like this, if the tissue is larger than the available imaging area, a contrast agent is administered to a part of the area of the tissue to capture time-series images of the area. This is repeated by moving the bed and securing it again. In other words, a contrast agent is administered more than once, and volume scan is performed by moving the imaging areas to photograph the entire area of the tissue in divided areas. The images may be captured such that some areas have an overlapping area.

One approach to obtain an image representing the entire tissue from images captured in divided areas is to select a vessel pixel that represents a blood vessel from pixels in each image, and associate vessel pixels thus selected as landmarks to thereby perform the registration of the images. The images after the registration form an image that represents an area including the entire tissue. In other words, registered partial images are combined together to obtain the entire area image.

The perfusion analysis requires transition information on an artery to be analyzed. However, in an image captured by capturing divided areas, an artery area may sometimes be specified in only a part of partial image areas. In this case, the perfusion analysis cannot be performed for tissue in the partial image where an artery area is not specified. This cannot be solved even by combining a plurality of partial images using a known technique. This is because the images of divided areas are captured at different times, and therefore, the transition information of an artery obtained from an artery area specified in a part of the partial images cannot be applied to those in which an artery area is not specified.

Further, in the perfusion analysis, the transition is analyzed in the pixel value representing the concentration of a contrast agent administered to capture time-series images. However, when time-series images are captured by moving the imaging area with two or more doses of a contrast agent, the contrast agent administered previous to a particular time-series image may remain in the area represented in the time-series images. In this case, transition occurs in the concentration of the contrast agent administered to photograph the time-series image and that of the contrast agent administered previous to the capturing, and thus the transition of a pixel value representing the sum of the concentrations is analyzed. This reduces the accuracy of the perfusion analysis.

DETAILED DESCRIPTION

In general, according to one embodiment, a medical image analyzer is configured to analyze time-series images of a subject to obtain hemodynamics of the subject. The medical image analyzer includes a retriever, a first artery transition information unit, a vessel pixel selector, a blood vessel transition information unit, an image association unit, and a second artery transition information unit. The retriever retrieves a plurality of time-series images captured of a plurality of areas of a subject having been administered a contrast agent at different times. The first artery transition information unit obtains first artery transition information that represents the transition of the pixel value in an artery area based on the artery area specified in a part of the time-series images. The vessel pixel selector selects vessel pixels each representing a blood vessel from pixels of the time-series images. The blood vessel transition information unit obtains blood vessel transition information that represents the transition of the pixel value of the vessel pixels selected by the vessel pixel selector. The image association unit obtains a correspondence relationship between one and another of the time-series images. The second artery transition information unit obtains second artery transition information corresponding to the artery area at the time of capturing time-series images other than the part of the time-series images based on time information indicating the time of capturing each of the time-series images, the first artery transition information obtained by the first artery transition information unit, the blood vessel transition information obtained by the blood vessel transition information unit, and the correspondence relationship obtained by the image association unit.

First Embodiment

Figure 1:
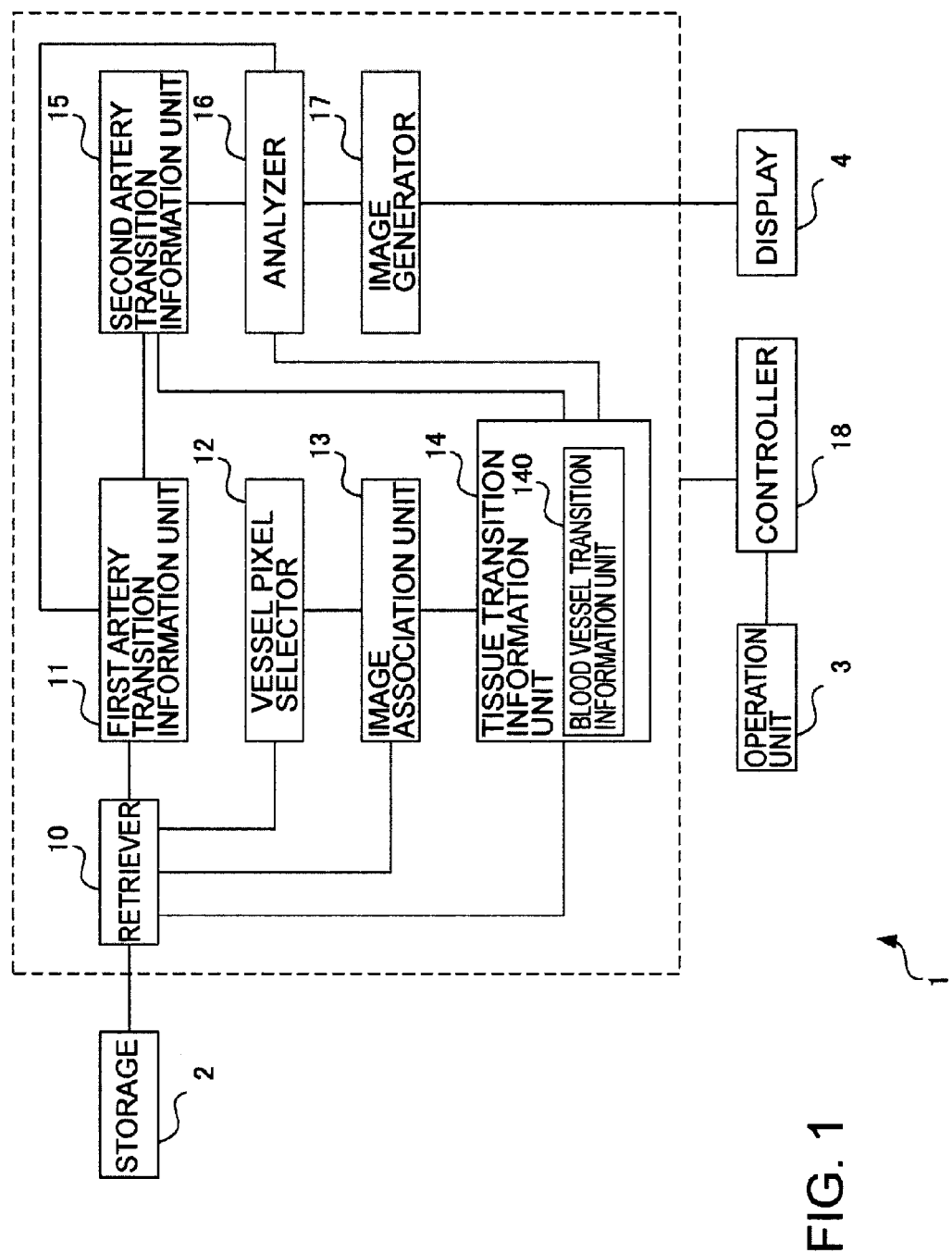
FIG. 1 is a functional block diagram illustrating an example of the configuration of a medical image analyzer according to an embodiment.

With reference to FIG. 1, a description is given of an example of the configuration of a medical image analyzer 1 according to a first embodiment. The medical image analyzer 1 is configured to analyze time-series images of a subject to obtain the hemodynamics of the subject.

A retriever 10 retrieves, from a storage 2, a plurality of time-series images captured of a plurality of areas of a subject who has been administered a contrast agent at different times. The time-series images may be captured to have an overlapping area. The retriever 10 further retrieves, from the storage 2, an entire area image representing all areas of the subject, to which the contrast agent is not administered. Here, the time-series images correspond to a moving image in which a plurality of still images (frames) captured of one area of the subject at regular intervals are correlated in time-series. When a plurality of areas of the subject is photographed in time-series, naturally, a plurality of time-series images are obtained. The entire area image is, for example, a still image captured by a helical scan using an X-ray CT apparatus. The time-series images and the entire area image are stored in the storage 2 located inside or outside of the medical image analyzer 1. When the storage 2 is located outside of the medical image analyzer 1, the retriever 10 retrieves the time-series images and the entire area image from the storage 2 via a common communication means.

Figure 2:
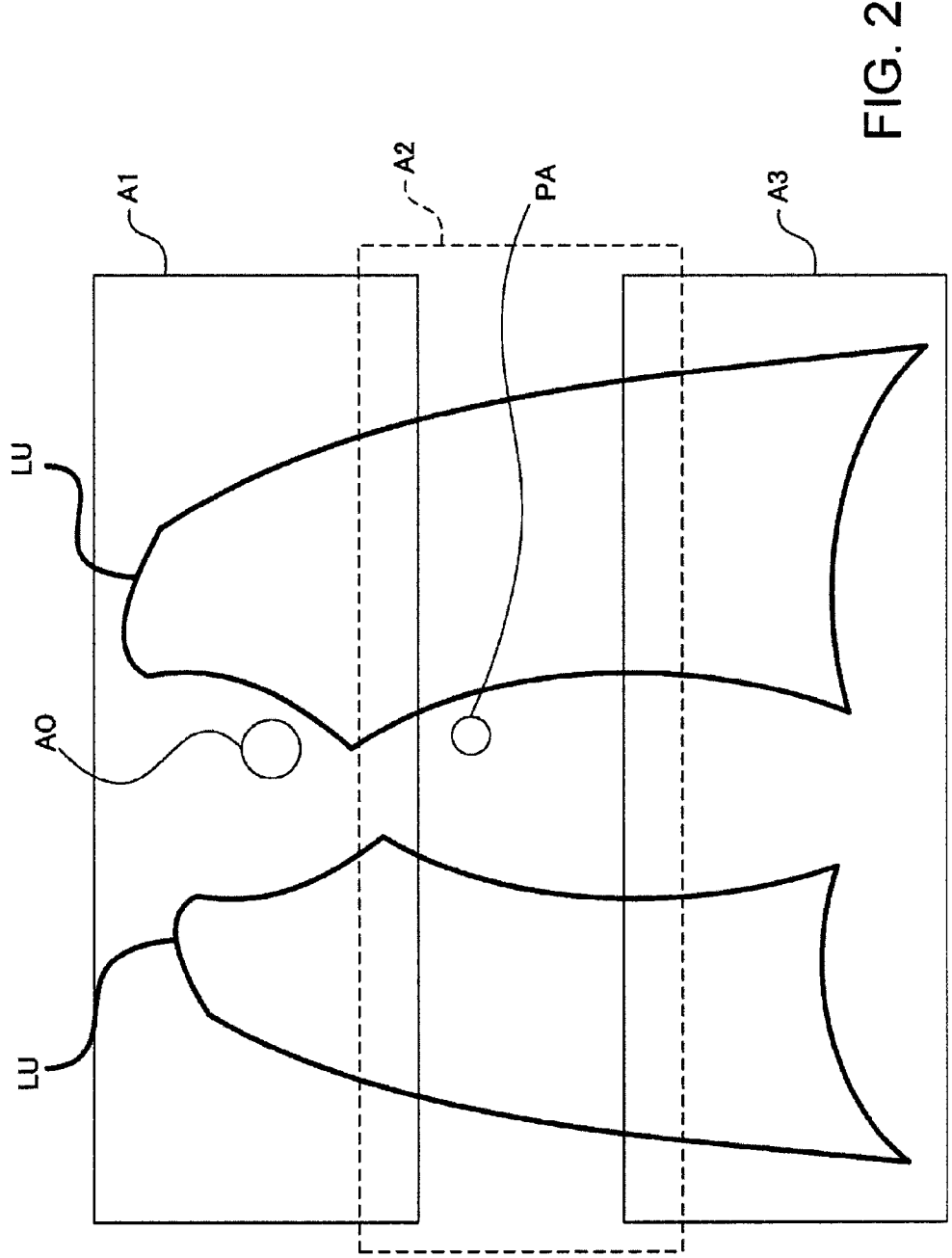
FIG. 2 is a schematic diagram illustrating the outline of the medical image analyzer of the embodiment.

A first artery transition information unit 11 obtains first artery transition information that represents the transition of pixel values in an artery area based on the artery area specified in a part of the time-series images retrieved by the retriever 10. In other words, the first artery transition information unit 11 obtains transition information on the concentration of the contrast agent (density of contrast) in a position of the subject represented by the artery area. As an example of this process, the first artery transition information unit 11 calculates the average of the pixel values of pixels in the artery area in each frame, and obtains the time-series variation of the average value as the transition information. The artery area refers to an area that represents a blood inflow pathway to the tissue to be analyzed in the time-series images. For example, when the tissue is the brain, an area where the cerebral artery is represented is the artery area. When the tissue is the liver, an area representing the portal vein as well as an area representing the hepatic artery is the artery area. Although the portal vein is not an artery, it is regarded herein as the artery area for convenience. Besides, the lungs have two arteries, i.e., the pulmonary artery and the bronchial artery, as the blood inflow pathway. When the tissue is the lungs, generally, it is difficult to specify an area in which the bronchial artery is represented as the artery area. Therefore, an area where the aorta is represented in place of the bronchial artery is specified as the artery area. In addition, the area where the pulmonary artery is represented is specified as the artery area. Since the time-series images are captured by dividing the entire area of the tissue into a plurality of areas, the artery area is not always specified in all of them. Accordingly, the artery area is specified in a part of the time-series images, i.e., time-series images captured by capturing a part of the area of the tissue. As a result, the time-series images includes those in which the artery area is specified (time-series images captured by capturing an area that includes the artery area) and those in which the artery area is not specified (time-series images captured by capturing an area that includes no artery area). For example, the user specifies the artery area by using an operation unit 3 while viewing a certain frame. For another example, the first artery transition information unit 11 may automatically specify the artery area with reference to clinical statistical data. FIG. 2 is a schematic diagram illustrating an example in which a plurality of time-series images is captured of the lungs of the subject as the tissue to be analyzed. In this example, among time-series images captured by capturing first area A1, second area A2 and third area A3 obtained by dividing lungs LU into three areas, an area where the aorta is represented is specified as an artery area AO of the aorta in a time-series image captured of the first area A1. In addition, an area where the pulmonary artery is represented is specified as an artery area PA of the pulmonary artery in a time-series image captured of the second area A2. Incidentally, the time-series images captured of the first area A1, the second area A2, and the third area A3 are referred to as first time-series image, second time-series image, and third time-series image, respectively.

A vessel pixel selector 12 selects a vessel pixel that represents a blood vessel from among pixels of the time-series images retrieved by the retriever 10. For example, the vessel pixel selector 12 selects a pixel representing a branch point of a blood vessel from among the pixels of the time-series images as the vessel pixel. The vessel pixel selector 12 may select a vessel pixel by, for example, the method disclosed in Hidenori Shikata et al. "An algorithm for localizing branch points of pulmonary vessels for non-rigid registration of the lungs" IEICE Trans. Vol. J85-D-11, No. 10, pp. 1613-1623, 2002. For example, the vessel pixel selector 12 creates a graph of blood vessels of the tissue, and obtains a branch point in the graph. The vessel pixel selector 12 performs a distance transform in a certain area in the vicinity of the branch point, and obtains a product set area regarding each branch in the certain area as a cylinder. The vessel pixel selector 12 selects a pixel corresponding to the center of gravity of the product set area as a vessel pixel.

Further, the vessel pixel selector 12 selects an entire area vessel pixel that represents a blood vessel from among pixels of the entire area image retrieved by the retriever 10. For example, by the method described above, the vessel pixel selector 12 selects a pixel representing a branch point of a blood vessel from among the pixels of the time-series images as the vessel pixel. In addition, the vessel pixel selector 12 selects a pixel representing a branch point of a blood vessel from among the pixels of the entire area image as the entire area vessel pixel. The vessel pixel selector 12 sends the pixels to an image association unit 13.

Still further, the vessel pixel selector 12 newly selects a first overlapping area vessel pixel that represents a blood vessel from among pixels of an area corresponding to an overlapping area in the entire area image specified by the image association unit 13 (described later) at a higher density than the entire area vessel pixel associated therewith by the image association unit 13. The vessel pixel selector 12 newly selects a second overlapping area vessel pixel that represents a blood vessel from among pixels in the overlapping area of the time-series images at a higher density than the vessel pixels. The image association unit 13 associates the vessel pixel with the entire area vessel pixel selected by the vessel pixel selector 12. If this mapping is difficult or higher mapping accuracy is desired, the mapping accuracy needs to be increased. In this case, after the image association unit 13 has specified an area (corresponding area) corresponding to the overlapping area in the entire area image (registration is performed between the entire area image and the time-series images), the vessel pixel selector 12 further selects a pixel that represents a blood vessel from among pixels of the corresponding area as a first overlapping area vessel pixel. The vessel pixel selector 12 also selects a pixel that represents a blood vessel from among pixels in the overlapping area of the time-series images as a second overlapping area vessel pixel. At this time, the vessel pixel selector 12 selects the pixels in the corresponding area and the overlapping area at a higher density than the entire area vessel pixel and the vessel pixel after a vessel association unit has specified the corresponding area, and sends them to the image association unit 13. Thereby, the first overlapping area vessel pixel and the second overlapping area vessel pixel are added as pixels to be associated for the registration between the entire area image and the time-series images.

The image association unit 13 obtains a correspondence relationship between one and another of the time-series images. For example, among vessel pixels selected by the vessel pixel selector 12, the image association unit 13 associates a vessel pixel in the overlapping area in one of the time-series images with a vessel pixel in the same overlapping area in another as having a correspondence relationship with each other. The image association unit 13 may associate the vessel pixels with each other by, for example, the method disclosed in Japanese Unexamined Patent Application Publication No. 2008-43736. For example, the image association unit 13 excludes some vessel pixels based on the distances between any two of the vessel pixels as landmarks or angles of a polygon formed by any three or more of them, and associates remaining vessel pixels. That is, the image association unit 13 compares the distance and angle as described above between a vessel pixel in the overlapping area in one of the time-series images and a vessel pixel in the same overlapping area in another, and associates them with each other.

Besides, by associating the vessel pixel and the entire area vessel pixel selected by the vessel pixel selector 12, the image association unit 13 associates a vessel pixel in the overlapping area in one of the time-series images with a vessel pixel in the overlapping area in another as having a correspondence relationship with each other, and specifies a vessel pixel in the area corresponding to the overlapping area in the entire area image. For another example, the image association unit 13 first performs registration between each of the time-series images and the entire area image. Since the entire area image includes all areas of the time-series images, the time-series images are positioned to one another by this registration. With this positioning of the time-series images each matched with the entire area image, the image association unit 13 associates a vessel pixel in the entire area image with a vessel pixel in the time-series images. Thus, the image association unit 13 can specify a vessel pixel in the area corresponding to the overlapping area.

Further, when performing mapping with higher accuracy, after the vessel pixel selector 12 has newly selected the first overlapping area pixel and the second overlapping area pixel, the image association unit 13 associates a part of first overlapping area vessel pixels with a part of second overlapping area vessel pixels. Thereby, the image association unit 13 associates a vessel pixel in the overlapping area in one of the time-series images with a vessel pixel in the same overlapping area in another as having a correspondence relationship with each other. After the vessel pixel selector 12 adds the pixels to be associated for the registration between the entire area image and the time-series images, the image association unit 13 further performs registration. Thereby, the image association unit 13 can perform the registration with higher accuracy than before the pixels are added.

Having associated a part of the first overlapping area vessel pixels with a part of the second overlapping area vessel pixels newly selected by the vessel pixel selector 12, the image association unit 13 compares a first peripheral image with a second peripheral image. The first peripheral image is an image of an area including first unassociated pixels, i.e., pixels in the first overlapping area vessel pixels, which are not associated with the second overlapping area vessel pixels. The second peripheral image is an image of an area including second unassociated pixels, i.e., pixels corresponding to a peripheral image in the time-series images. When the degree of coincidence between the first peripheral image and the second peripheral image exceeds a specified value, by further associating the first unassociated pixels and the second unassociated pixels, the image association unit 13 associates a vessel pixel in the overlapping area in one of the time-series images with a vessel pixel in the overlapping area in another as having a correspondence relationship with each other. In other words, the image association unit 13 compares peripheral images of pixels (the first unassociated pixels and the second unassociated pixels) which have not been employed as landmarks using a general image correlation method. When the degree of coincidence between the first peripheral image and the second peripheral image exceeds a specified value, the image association unit 13 associates the first unassociated pixels in the first peripheral image with the second unassociated pixels in the second peripheral image. Incidentally, the user may specify the range of the first and second peripheral images using the operation unit 3, or the range may be preset in the image association unit 13.

A tissue transition information unit 14 receives the time-series images retrieved by the retriever 10 and obtains tissue transition information that represents a time-series change in the pixel value in the tissue of the subject. The tissue transition information unit 14 associates pixels between a plurality of frames of the time-series images, and obtains transition information indicating a time-series change in the pixel value of each pixel. In other words, the tissue transition information unit 14 obtains information indicating the transition of the concentration of the contrast agent in the tissue of the subject.

A blood vessel transition information unit 140 obtains blood vessel transition information that represents the transition of the pixel values of the vessel pixels selected by the vessel pixel selector 12. For example, among vessel pixels selected by the vessel pixel selector 12, the blood vessel transition information unit 140 obtains the transition of the pixel values of vessel pixels associated by the image association unit 13 as the blood vessel transition information. In other words, the blood vessel transition information unit 140 associates vessel pixels between a plurality of frames, and obtains information indicating a time-series change in the pixel value of each pixel as the blood vessel transition information. Thereby, the blood vessel transition information unit 140 obtains transition information indicating the transition of the concentration of the contrast agent in a blood vessel represented by the vessel pixels.

A second artery transition information unit 15 obtains second artery transition information based on time information indicating the time of capturing each of the time-series images, the first artery transition information obtained by the first artery transition information unit 11, the blood vessel transition information obtained by the blood vessel transition information unit 140, and the correspondence relationship obtained by the image association unit 13. The second artery transition information corresponds to an artery area at the time of capturing time-series images other than those where the artery area is set. The second artery transition information indicates the transition of the concentration of the contrast agent in a position of the subject represented by an artery area specified in another area at the time of capturing time-series images related to areas where an artery area is not specified. In the example of a time-series image captured of the first area A1 illustrated in FIG. 2, the second artery transition information indicates the transition of the concentration of the contrast agent in a position of the subject represented by the artery area PA of the pulmonary artery specified in the second area A2 at the time of capturing the time-series image. In the example of a time-series image captured of the second area A2, the second artery transition information indicates the transition of the concentration of the contrast agent in a position of the subject represented by the artery area AO of the aorta specified in the first area A1 at the time of capturing the time-series image. In the example of a time-series image captured of the third area A3, the second artery transition information indicates the transition of the concentration of the contrast agent in a position of the subject represented by each of the artery area AO and the artery area PA at the time of capturing the time-series image.

Figure 3:
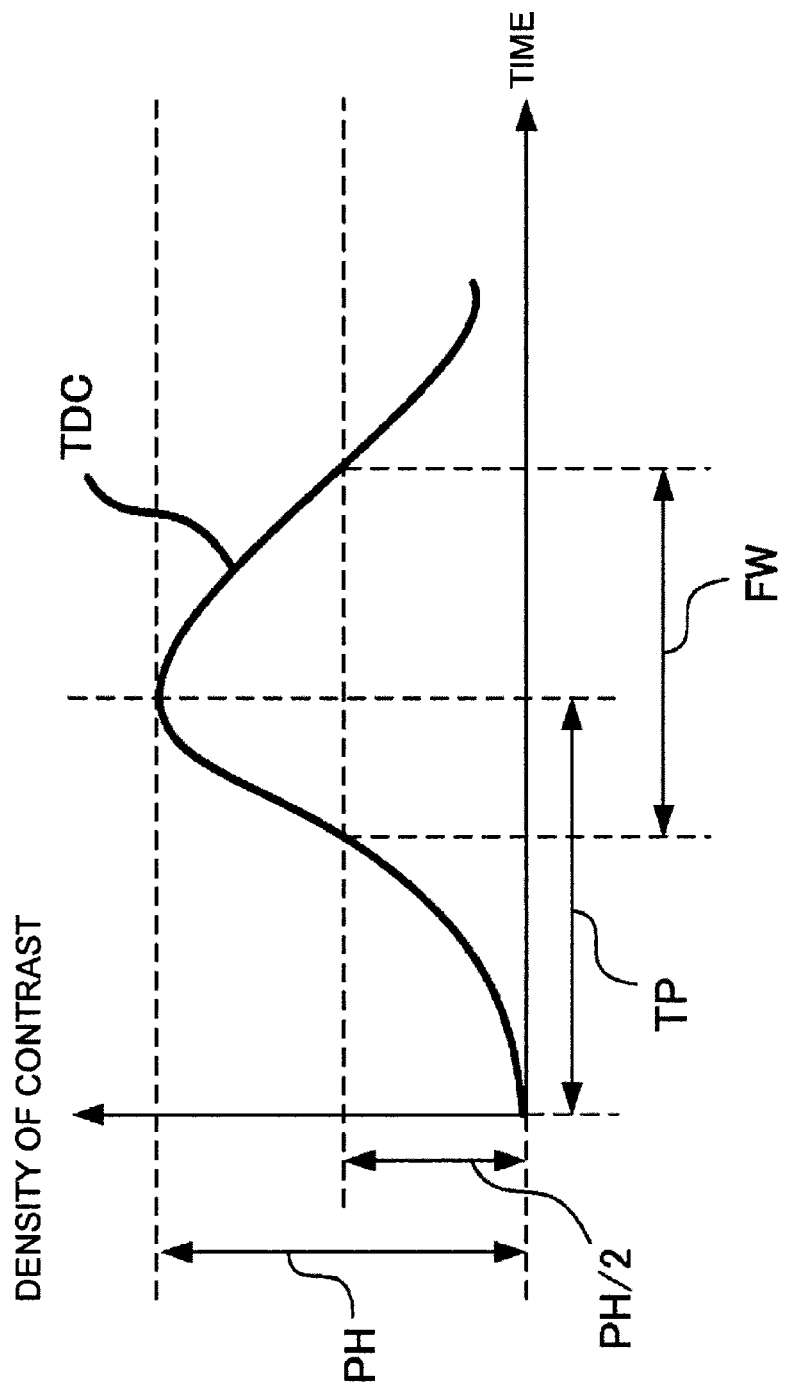
FIG. 3 is a schematic diagram illustrating the outline of the medical image analyzer of the embodiment.

The second artery transition information unit 15 stores in advance blood vessel classification information that represents the characteristics of each type of blood vessel. The second artery transition information unit 15 determines the type of the blood vessel represented by the vessel pixels associated by the image association unit 13 based on the blood vessel transition information obtained by the blood vessel transition information unit 140 and the blood vessel classification information. The second artery transition information unit 15 includes the blood vessel type thus determined in the blood vessel transition information to obtain the second artery transition information. The blood vessel classification information is, for example, information representing the characteristics of the time density curve of each blood vessel type such as the pulmonary artery and the bronchial artery. FIG. 3 is a schematic diagram illustrating an example of the characteristics of a time density curve TDC. Examples of the characteristics of the time density curve TDC include peak height (PH), curve width (full width at half maximum: FW), peak time (time to peak: TP) and the like. These characteristics are known to be different among blood vessel types. The second artery transition information unit 15 compares the blood vessel classification information stored in advance with the time density curve of the blood vessel transition information to determine the type of the blood vessel represented by the vessel pixel of the blood vessel transition information. For example, if the lungs are to be analyzed, the second artery transition information unit 15 determines the type of each blood vessel represented by the vessel pixels associated by the image association unit 13 as the pulmonary artery, the bronchial artery, or another type (neither the bronchial artery nor the pulmonary artery).

The second artery transition information unit 15 determines the type of the blood vessel represented by the vessel pixels associated by the image association unit 13, thereby obtaining the correspondence between vessel pixels in the overlapping area. For example, in the case of the imaging area of FIG. 2, the overlapping area between the first area A1 and the second area A2, transition information $C1l\_pa\_i(t)$ ($i=1$ to $N12\_pa$) of the pixel value of the vessel pixel representing a blood vessel that has been determined as the pulmonary artery in the first time-series image is associated with transition information $C2u\_pa\_i(t)$ ($i=1$ to $N12\_pa$) of the pixel value of the vessel pixel representing a blood vessel that has been determined as the pulmonary artery in the second time-series image. Here, $N12\_pa$ indicates the number of vessel pixels that have been associated in the overlapping area between the first area A1 and the second area A2, and also determined as the pulmonary artery. Besides, in the overlapping area between the first area A1 and the second area A2, transition information $C1l\_ba\_i(t)$ ($i=1$ to $N12\_ba$) of the pixel value of the vessel pixel representing a blood vessel that has been determined as the bronchial artery in the first time-series image is associated with transition information $C2u\_ba\_i(t)$ ($i=1$ to $N12\_ba$) of the pixel value of the vessel pixel representing a blood vessel that has been determined as the pulmonary artery in the second time-series image. Here, $N12\_ba$ indicates the number of vessel pixels that have been associated in the overlapping area between the first area A1 and the second area A2, and also determined as the bronchial artery. Further, in the overlapping area between the second area A2 and the third area A3, transition information $C2l\_pa\_i(t)$ ($i=1$ to $N23\_pa$) of the pixel value of the vessel pixel representing a blood vessel that has been determined as the pulmonary artery in the second time-series image is associated with transition information C3u_pa_i (t) (i=1 to N23_pa) of the pixel value of the vessel pixel representing a blood vessel that has been determined as the pulmonary artery in the third time-series image. Here, N23_pa indicates the number of vessel pixels that have been associated in the overlapping area between the second area A2 and the third area A3, and also determined as the pulmonary artery. Also, in the overlapping area between the second area A2 and the third area A3, transition information C2l_ba_i (t) (i=1 to N23_ba) of the pixel value of the vessel pixel representing a blood vessel that has been determined as the bronchial artery in the second time-series image is associated with transition information C3u_ba_i (t) (i=1 to N23_ba) of the pixel value of the vessel pixel representing a blood vessel that has been determined as the pulmonary artery in the third time-series image. Here, N23_ba indicates the number of vessel pixels that have been associated in the overlapping area between the second area A2 and the third area A3, and also determined as the bronchial artery.

Figure 4:
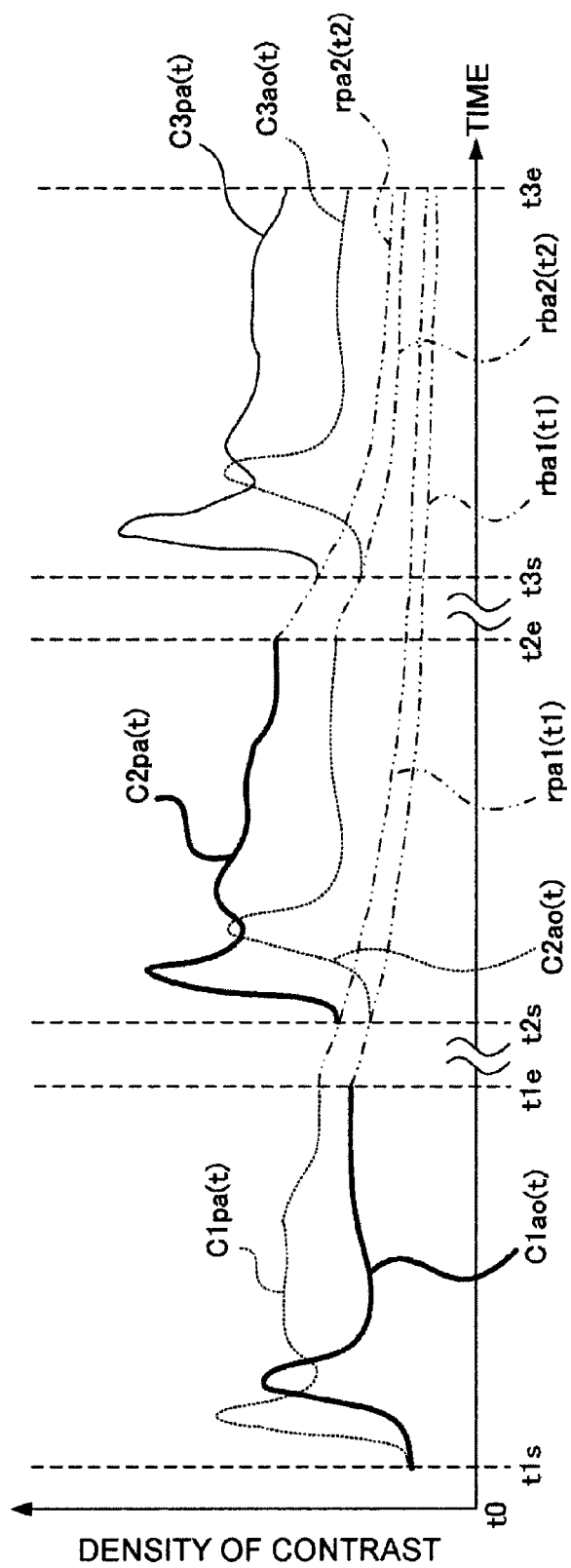
FIG. 4 is a schematic diagram illustrating the outline of the medical image analyzer of the embodiment.

FIG. 4 is a schematic diagram illustrating the time density curve obtained by the capturing as illustrated in FIG. 2. The horizontal axis represents time and the vertical axis represents pixel value. In FIG. 4, the time density curve C1ao(t) of the artery area AO of the aorta is obtained in a period from capturing start time t1s to capturing end time t1e of the first time-series image. The time density curve C2pa(t) of the artery area PA of the pulmonary artery is obtained in a period from capturing start time t2s to capturing end time t2e of the second time-series image. The time density curve of none of the arteries is obtained in a period from capturing start time t3s to capturing end time t3e of the third time-series image. Described below is how the second artery transition information unit 15 obtains the second artery transition information in each time-series image in the example of FIG. 4.

The second artery transition information unit 15 corrects the time deviation between the contrast agent administration time and the capturing start time for each time-series image by, for example, the following equations:

$$t1 = t-s1-t1s : t1s \le t \le t1e$$

$$t2 = t-s2-t2s : t2s \le t \le t2e$$

$$t3 = t-s3-t3s : t3s \le t \le t3e \quad \text{[Equations 1]}$$

where t is the time that has elapsed from the reference time t0, s1 is the time deviation of the first time-series image, s2 is the time deviation of the second time-series image, and s3 is the time deviation of the third time-series image.

In Equations 1, s1, s2 and s3 are unknown. The second artery transition information unit 15 represents the attenuation curve of the pulmonary artery and the attenuation curve of the bronchial artery by, for example, the following equations:

$$rpa1(x) = Dpa(T)\exp\left(-\frac{x-t1e}{T1}\right) : x > t1e$$

$$rba1(x) = Dba(T)\exp\left(-\frac{x-t1e}{T1}\right) : x > t1e$$

$$rpa2(x) = Dpa(T)\exp\left(-\frac{x-t2e}{T2}\right) : x > t2e$$

$$rba2(x) = Dba(T)\exp\left(-\frac{x-t2e}{T2}\right) : x > t2e \quad \text{[Equations 2]}$$

where T1 and T2 are the time constant of attenuation.

In Equations 2, function values rpa1(x), rba1(x), rpa2(x), and rba2(x) are assumed to be zero in the outside of the range of x. T is the capturing time for each area. That is, T=t1e−t1s=t2e−t2s=t3e−t3s. T1 and T2 are unknown. Besides, Dpa(t) and Dba(t) are time density curves for the pulmonary artery and the bronchial artery, which do not include the influence of circulations after the secondary circulation, and are unknown, i.e., time density curves related to the concentration of only the contrast agent that has been administered to capture a single time-series image. In addition, the second artery transition information unit 15 represents the time density curve of the pulmonary artery Cpa(t) and the time density curve of the bronchial artery Cba(t) with respect to the capturing time of all the first, second, and third time-series images as the second artery transition information by, for example, the following equations:

$$Cpa(t) = a1 \times Dpa(t1) + a1 \times rpa1(t1) + a2 \times Dpa(t2) + a2 \times rpa2(t2) + a3 \times Dpa(t3)$$

$$Cba(t) = a1 \times Dba(t1) + a1 \times rba1(t1) + a2 \times Dba(t2) + a2 \times rba2(t2) + a3 \times Dba(t3) \quad \text{[Equations 3]}$$

Equations 3 indicate that the attenuation curve of Equations 2 is applied to Dpa(t) and Dba(t). In Equations 3, a1, a2 and a3 are unknown, and are coefficients to be multiplied to the attenuation curve. Further, a1, a2 and a3 are coefficients to correct for partial volume effect. If there is no need to correct the partial volume effect, they may be in the following relationship: a1=a2=a3=1. In addition, the second artery transition information unit 15 represents the time density curves of the pulmonary artery and the bronchial artery in the overlapping area by, for example, the following equations:

$$C1l_{pa}(t) = a1 \times Dpa(t1)$$

$$C1l_{ba}(t) = a1 \times Dba(t1)$$

$$C2u_{pa}(t) = a1 \times rpa(t) + a2 \times Dpa(t2)$$

$$C2u_{ba}(t) = a1 \times rba(t) + a2 \times Dba(t2)$$

$$C2l_{pa}(t) = a1 \times rpa1(t) + a2 \times Dpa(t2)$$

$$C2l_{ba}(t) = a1 \times rba1(t) + a2 \times Dba(t2)$$

$$C3u_{pa}(t) = a1 \times rpa1(t) + a2 \times rpa2(t) + a3 \times Dpa(t3)$$

$$C3u_{ba}(t) = a1 \times rba1(t) + a2 \times rpa2(t) + a3 \times Dba(t3) \quad \text{[Equations 4]}$$

In Equations 4, $C1l_{pa}(t)$ represents the time density curve of the pulmonary artery in the overlapping area between the first area A1 and the second area A2 in the first time-series image. $C1l_{ba}(t)$ represents the time density curve of the bronchial artery in the overlapping area between the first area A1 and the second area A2 in the first time-series image. $C2u_{pa}(t)$ represents the time density curve of the pulmonary artery in the overlapping area between the first area A1 and the second area A2 in the second time-series image. $C2u_{ba}(t)$ represents the time density curve of the bronchial artery in the overlapping area between the first area A1 and the second area A2 in the second time-series image. $C2l_{pa}(t)$ represents the time density curve of the pulmonary artery in the overlapping area between the second area A2 and the third area A3 in the second time-series image. $C2l_{ba}(t)$ represents the time density curve of the bronchial artery in the overlapping area between the second area A2 and the third area A3 in the second time-series image. $C3u_{pa}(t)$ represents the time density curve of the pulmonary artery in the overlapping area between the second area A2 and the third area A3 in the third time-series image. C3u$_{ba}$(t) represents the time density curve of the bronchial artery in the overlapping area between the second area A2 and the third area A3 in the third time-series image. Further, the second artery transition information unit 15 represents the time density curve of the artery area by, for example, the following equations:

$$C1pa(t)=Dpa(t1)$$

$$C1ao(t)=Dba(t1)$$

$$C2pa(t)=rpa1(t)+Dpa(t2)$$

$$C2ao(t)=rba1(t)+Dba(t2)$$

$$C3pa(t)=rpa1(t)+rpa2(t)+Dpa(t3)$$

$$C3ao(t)=rba1(t)+rba2(t)+Dba(t3) \quad \text{[Equations 5]}$$

In Equations 5, C1pa(t) is a time density curve that represents transition information of the pixel value of the pixel in the artery area PA when the artery area PA of the pulmonary artery is specified in the first area A1. C1ao(t) is a time density curve that represents transition information of the pixel value of the pixel in the artery area AO when the artery area AO of the aorta is specified in the first area A1. C2pa(t) is a time density curve that represents transition information of the pixel value of the pixel in the artery area PA when the artery area PA of the pulmonary artery is specified in the second area A2. C2ao(t) is a time density curve that represents transition information of the pixel value of the pixel in the artery area AO when the artery area AO of the aorta is specified in the second area A2. C3pa(t) is a time density curve that represents transition information of the pixel value of the pixel in the artery area PA when the artery area PA of the pulmonary artery is specified in the third area A3. C3ao(t) is a time density curve that represents transition information of the pixel value of the pixel in the artery area AO when the artery area AO of the aorta is specified in the third area A3. The second artery transition information unit 15 selects any of Equations 5 to be used based on the area where the artery area is specified. In the example of FIG. 2 in which the artery area AO of the aorta is specified in the first area A1, and the artery area PA of the pulmonary artery is specified in the second area A2, equation representing C1ao(t) and equation representing C2pa(t) are selected as each representing a known time density curve measured.

The second artery transition information unit 15 obtains the variables of a1, a2, a3, s1, s2, s3, T1 and T2, and also Dpa(t) and Dba(t) based on the system of equations consisting of equations selected from Equations 4 and 5. The system of equations becomes a linear equation for a1, a2 and a3, and a nonlinear equation for the other variables. The second artery transition information unit 15 first obtains a1, a2 and a3 by a linear equation. Then, the second artery transition information unit 15 obtains other variables using a general nonlinear optimization method for objective functions comprising a residual error as a1, a2 and a3 are known. At this time, the second artery transition information unit 15 may use a general regularization method as appropriate. The second artery transition information unit 15 may also use general heuristics approach. Incidentally, when the system of equations is not required to include all equations selected from Equations 4 and 5, the second artery transition information unit 15 may select necessary equations for the system of equations. In addition, one of s1, s2 and s3 may be a known value. For example, it may be possible that s1=0. The image association unit 13 may obtain the variables of a1, a2, a3, s1, s2 and s3 as the correspondence relationship between one and another of the time-series images.

The second artery transition information unit 15 substitutes Dpa(t) and Dba(t) and the variables of s1, s2, s3, T1 and T2 thus obtained into Equations 3. Besides, assuming a1, a2, and a3 to be 1, the second artery transition information unit 15 obtains the time density curve Cpa(t) of the pulmonary artery and the time density curve Cba(t) of the bronchial artery with respect to all the capturing times of the first time-series image, the second time-series image, and the third time-series image as follows:

$$Cpa(t)=Dpa(t1)+rpa1(t1)+Dpa(t2)+rpa2(t2)+Dpa(t3)$$

$$Cba(t)=Dba(t1)+rba1(t1)+Dba(t2)+rba2(t2)+Dba(t3) \quad \text{[Equations 6]}$$

Equations 6 represent transition information of the artery area over all the capturing times of the first time-series image, the second time-series image, and the third time-series image.

Besides, since Dpa(t) and Dba(t) are determined, unknown time density curve not selected from Equations 5 is obtained. In the example of FIG. 2, C1pa(t), C2ao(t), C3pa(t) and C3ao(t) are obtained. They correspond to second artery transition information of this embodiment.

An analyzer 16 performs perfusion analysis on each of the time-series images according to a specified analysis method based on the first artery transition information obtained by the first artery transition information unit 11, the second artery transition information obtained by the second artery transition information unit 15, and the tissue transition information obtained by the tissue transition information unit 14. Examples of the analysis method include deconvolution method and maximum slope method. The user may specify the analysis method using the operation unit 3, or it may be preset in the analyzer 16. For example, the analyzer 16 performs perfusion analysis with respect to each pixel of the time-series images according to the specified analysis method using C1pa(t) and C1ao(t) as input functions for the first time-series image, C2pa(t) and C2ao(t) as input functions for the second time-series image, and C3pa(t) and C3ao(t) as input functions for the third time-series image. The analyzer 16 feeds an image generator 17 with the blood flow dynamics, such as the blood-flow volume or blood volume of the tissue of the subject represented by each pixel, as an analysis result.

Having received the time-series images registered to each other by the image association unit 13 and the analysis result from the analyzer 16, the image generator 17 generates a map that represents the hemodynamics of the tissue of the subject. Examples of the map include a blood-flow volume map and a blood volume map which represent the blood-flow volume and blood volume of the tissue of the lungs, respectively. The image generator 17 displays the map on the display 4.

A controller 18 controls each unit of the medical image analyzer 1. The controller 18 includes, for example, a processor and a storage. Examples of the processor include a central processing unit (CPU), a graphic processing unit (GPU), and application specific integrated circuit (ASIC). The storage includes, for example, a read only memory (ROM), a random access memory (RAM), and a hard disc drive (HDD). The storage stores computer programs for implementing the functions of each unit of the medical image analyzer 1. The processor executes the computer programs to implement the above functions.

While being operated by the user, the operation unit 3 feeds each unit of the apparatus with a signal and information corresponding to the content of the operation. The operation unit 3 includes, for example, a keyboard, a mouse, a touch panel, and the like. The operation unit 3 is not necessarily provided as integrated with the medical image analyzer 1, and may be configured to feed the signal and information to each unit of the apparatus via a common interface.

The display 4 is a display device formed of, for example, a cathode ray tube (CRT) or a liquid crystal display (LCD). The display 4 is not necessarily provided as integrated with the medical image analyzer 1, and may be configured to display images via a common interface.

Figure 5:
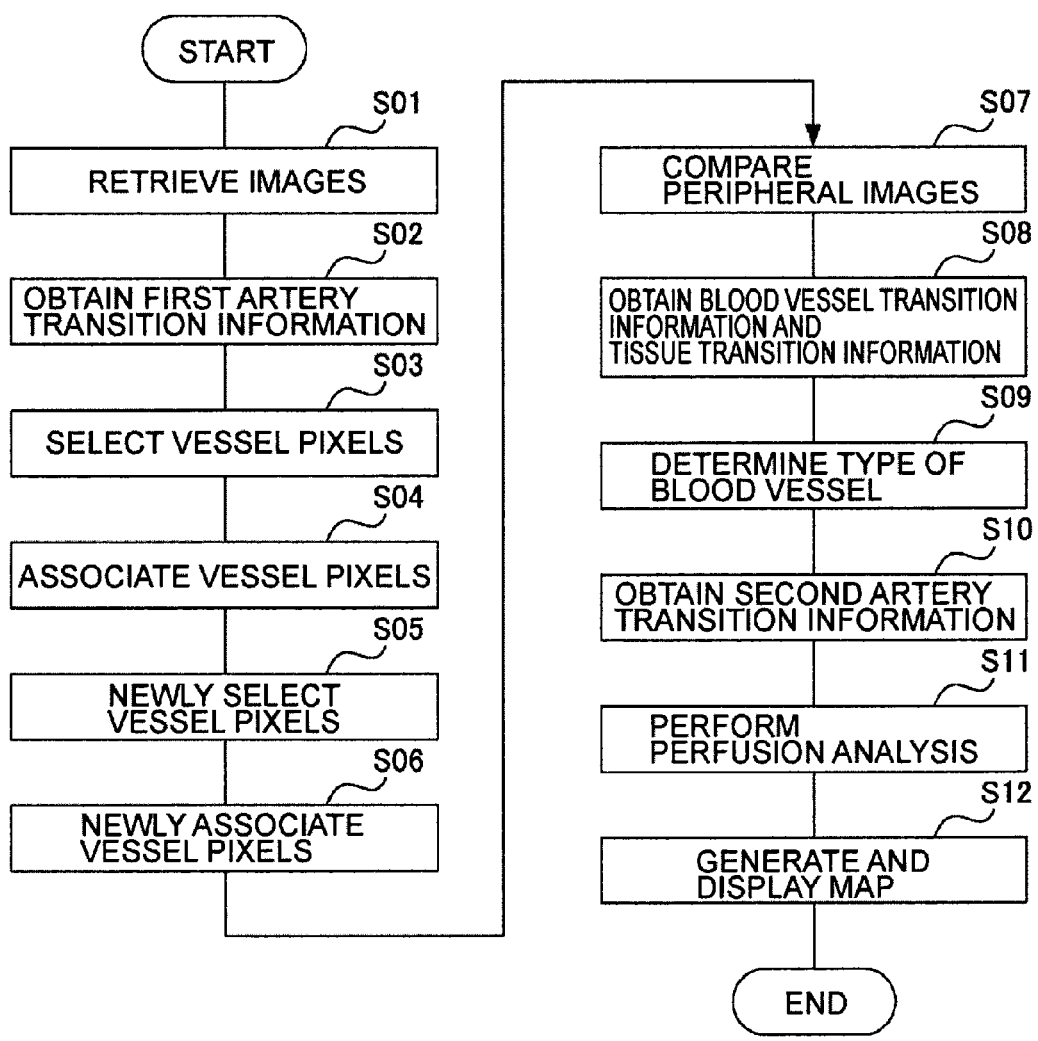
FIG. 5 is a flowchart of an example of the operation of the medical image analyzer of the embodiment.

Described below is the operation of the medical image analyzer 1 of this embodiment. FIG. 5 is a flowchart illustrating the operation of this embodiment.

S01: The retriever 10 retrieves, from the storage 2, a plurality of time-series images captured of a plurality of areas of a subject having been administered a contrast agent at different times such that the images have an overlapping area. The retriever 10 further retrieves, from the storage 2, an entire area image representing all the areas of the subject that has not been administered a contrast agent.

S02: The first artery transition information unit 11 obtains first artery transition information that represents the transition of the pixel value in an artery area based on the artery area specified in a part of the time-series images retrieved by the retriever 10.

S03: The vessel pixel selector 12 selects vessel pixels each representing a blood vessel from the pixels of the time-series images retrieved by the retriever 10. The vessel pixel selector 12 also selects an entire area vessel pixel representing a blood vessel from the pixels of the entire area image retrieved by the retriever 10.

S04: The image association unit 13 associates the vessel pixels with the entire area vessel pixel selected by the vessel pixel selector 12. Thereby, a vessel pixel in an overlapping area in one of the time-series images is associated with a vessel pixel in the overlapping area in another time-series image. The image association unit 13 specifies an area corresponding to the overlapping area in the entire area image.

S05: The vessel pixel selector 12 newly selects first overlapping area vessel pixels each representing a blood vessel from among pixels of the area corresponding to the overlapping area in the entire area image specified by the image association unit 13 at a higher density than the entire area vessel pixel associated therewith by the image association unit 13. In addition, the vessel pixel selector 12 newly selects second overlapping area vessel pixels each representing a blood vessel from among pixels in the overlapping area of the time-series images at a higher density than the vessel pixels.

S06: The image association unit 13 associates a part of the first overlapping area vessel pixels with a part of the second overlapping area vessel pixels. Thereby, the vessel pixel in the overlapping area in one of the time-series images is associated with the vessel pixel in the overlapping area in another time-series image.

S07: The image association unit 13 compares a first peripheral image with a second peripheral image. The first peripheral image is an image of an area including first unassociated pixels, i.e., pixels in the first overlapping area vessel pixels, which are not associated with the second overlapping area vessel pixels. The second peripheral image is an image of an area including second unassociated pixels, i.e., pixels corresponding to a peripheral image in the time-series images. When the degree of coincidence between the first peripheral image and the second peripheral image exceeds a specified value, the image association unit 13 further associates the first unassociated pixels and the second unassociated pixels.

S08: The blood vessel transition information unit 140 obtains blood vessel transition information that represents the transition of the pixel value of the vessel pixels associated by the image association unit 13. Besides, having received the time-series images retrieved by the retriever 10, the tissue transition information unit 14 obtains tissue transition information that represents a time-series change in the pixel value in the tissue of the subject.

S09: The second artery transition information unit 15 stores in advance blood vessel classification information that represents the characteristics of each type of blood vessel. The second artery transition information unit 15 determines the type of the blood vessel represented by the vessel pixels associated by the image association unit 13 based on the blood vessel transition information obtained by the blood vessel transition information unit 140 and the blood vessel classification information.

S10: The second artery transition information unit 15 obtains second artery transition information based on time information indicating the time of capturing each of the time-series images, the first artery transition information obtained by the first artery transition information unit 11, the blood vessel transition information obtained by the blood vessel transition information unit 140, and the correspondence relationship obtained by the image association unit 13. The second artery transition information corresponds to an artery area at the time of capturing time-series images other than those where the artery area is set.

S11: The analyzer 16 performs perfusion analysis on each of the time-series images according to a specified analysis method based on the first artery transition information obtained by the first artery transition information unit 11, the second artery transition information obtained by the second artery transition information unit 15, and the tissue transition information obtained by the tissue transition information unit 14.

S12: Having received the time-series images registered to each other by the image association unit 13 and the analysis result from the analyzer 16, the image generator 17 generates a map that represents the hemodynamics of the tissue of the subject. The image generator 17 displays the map on the display 4.

According to the first embodiment, the medical image analyzer 1 analyzes time-series images of a subject to obtain the hemodynamics of the subject. The medical image analyzer 1 includes the retriever 10, the first artery transition information unit 11, the vessel pixel selector 12, the image association unit 13, the blood vessel transition information unit 140, and the second artery transition information unit 15. The retriever 10 is configured to retrieve a plurality of time-series images captured of a plurality of areas of a subject having been administered a contrast agent at different times to have an overlapping area. The first artery transition information unit 11 is configured to obtain first artery transition information that represents a transition of pixel value in an artery area based on the artery area specified in a part of the time-series images. The vessel pixel selector 12 is configured to select vessel pixels each representing a blood vessel from pixels of the time-series images. The image association unit 13 is configured to associate, among the vessel pixels selected by the vessel pixel selector 12, a vessel pixel in the overlapping area in one of the time-series images with a vessel pixel in the overlapping area in another of the time-series images. The blood vessel transition information unit 140 is configured to obtain blood vessel transition information that represents a transition of pixel value of the vessel pixels associated by the image association unit 13. The second artery transition information unit 15 is configured to obtain second artery transition information corresponding to an artery area at a time of capturing time-series images other than the part of the time-series images based on time information indicating a time of capturing each of the time-series images, the first artery transition information obtained by the first artery transition information unit 11, and the blood vessel transition information obtained by the blood vessel transition information unit 140. Thereby, the medical image analyzer 1 can perform perfusion analysis on the time-series images where an artery area is not specified using the second artery transition information as an input function. Thus, the medical image analyzer 1 can perform perfusion analysis on an image where an artery area is not specified among images of a subject having been administered a contrast agent a plurality of times captured by moving the imaging area.

Second Embodiment

Figure 6:
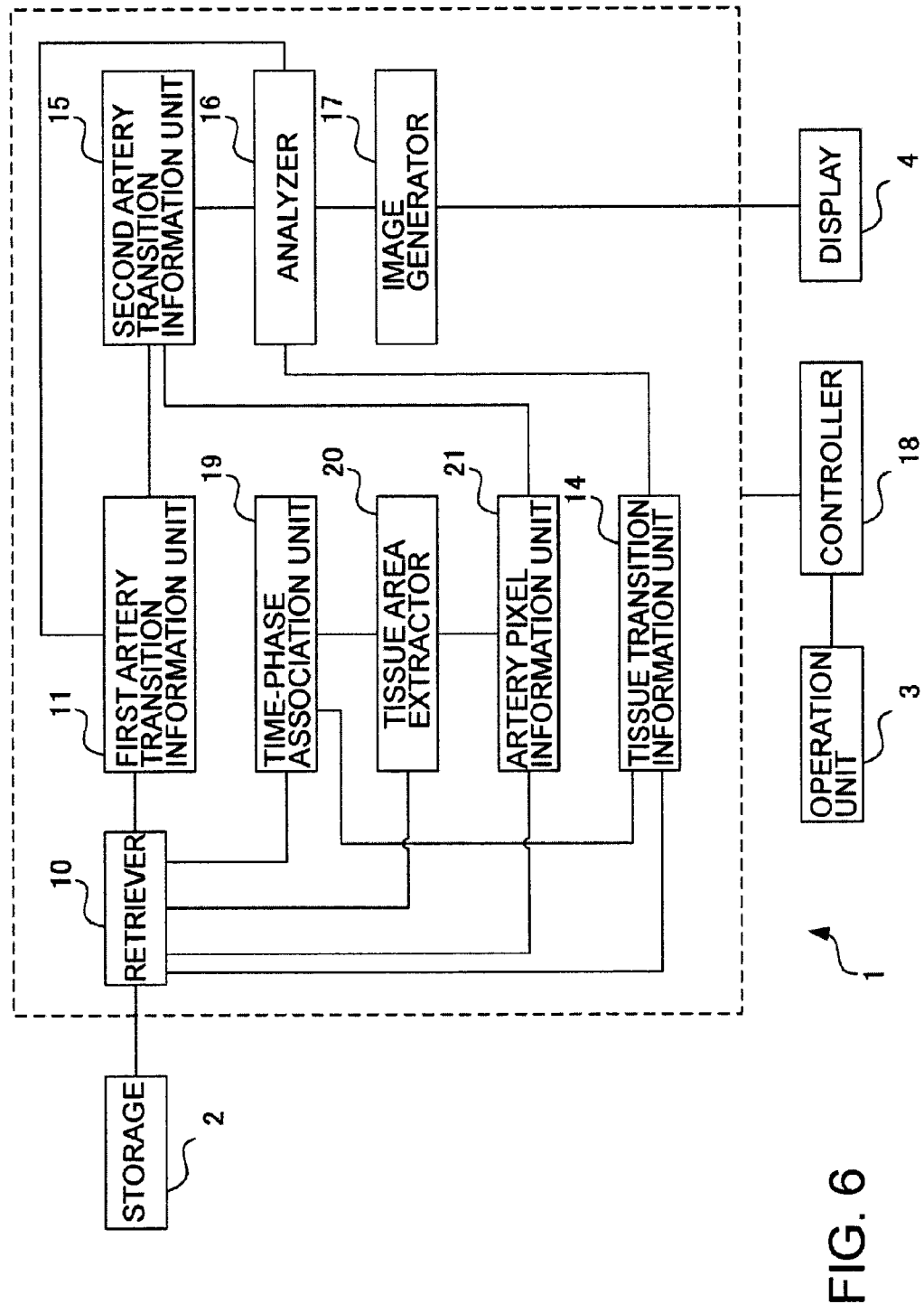
FIG. 6 is a functional block diagram illustrating an example of the configuration of a medical image analyzer according to another embodiment.

With reference to FIG. 6, a description is given of the configuration of the medical image analyzer 1 according to a second embodiment. The medical image analyzer 1 of this embodiment differs from that of the first embodiment in a time-phase association unit 19, the first artery transition information unit 11, a tissue area extractor 20, an artery pixel information unit 21, and the second artery transition information unit 15. The constituent elements are otherwise identical to those of the first embodiment. In the following, the differences from the first embodiment are mainly described. Besides, as illustrated in FIG. 7, an example is described in which the pulmonary artery area PA, which represents the origin of the pulmonary artery, is specified in the first area A1 and outside the second area A2.

The time-phase association unit 19 performs registration between pixels in frames of the time-series images retrieved by the retriever 10. For example, the time-phase association unit 19 performs registration between the one frame and another by image correlation processing. The time-phase association unit 19 performs the registration from the first frame to the last frame of the time-series images. Thereby, even if tissue moves due to breathing during the capturing of the time-series images, the tissue in one frame can be associated with that in another frame. The time-phase association unit 19 performs this mapping for each of the time-series images, and outputs the result as time-phase association information to the artery pixel information unit 21.

The first artery transition information unit 11 obtains first artery transition information that represents the transition of pixel values in an artery area based on the artery area specified in a part of the time-series images retrieved by the retriever 10. For example, the first artery transition information unit 11 calculates the average of the pixel values of pixels in the artery area PA of the pulmonary artery specified in the first area A1, and obtains information indicating the time variation of the average value as the first artery transition information. It is assumed that the first artery transition information C1pa(t): t1s≤t≤t1e, where t1s indicates the capturing start time at which the capturing of the first time-series image starts, and t1e indicates the capturing end time at which the capturing of the first time-series image ends.

Figure 7:
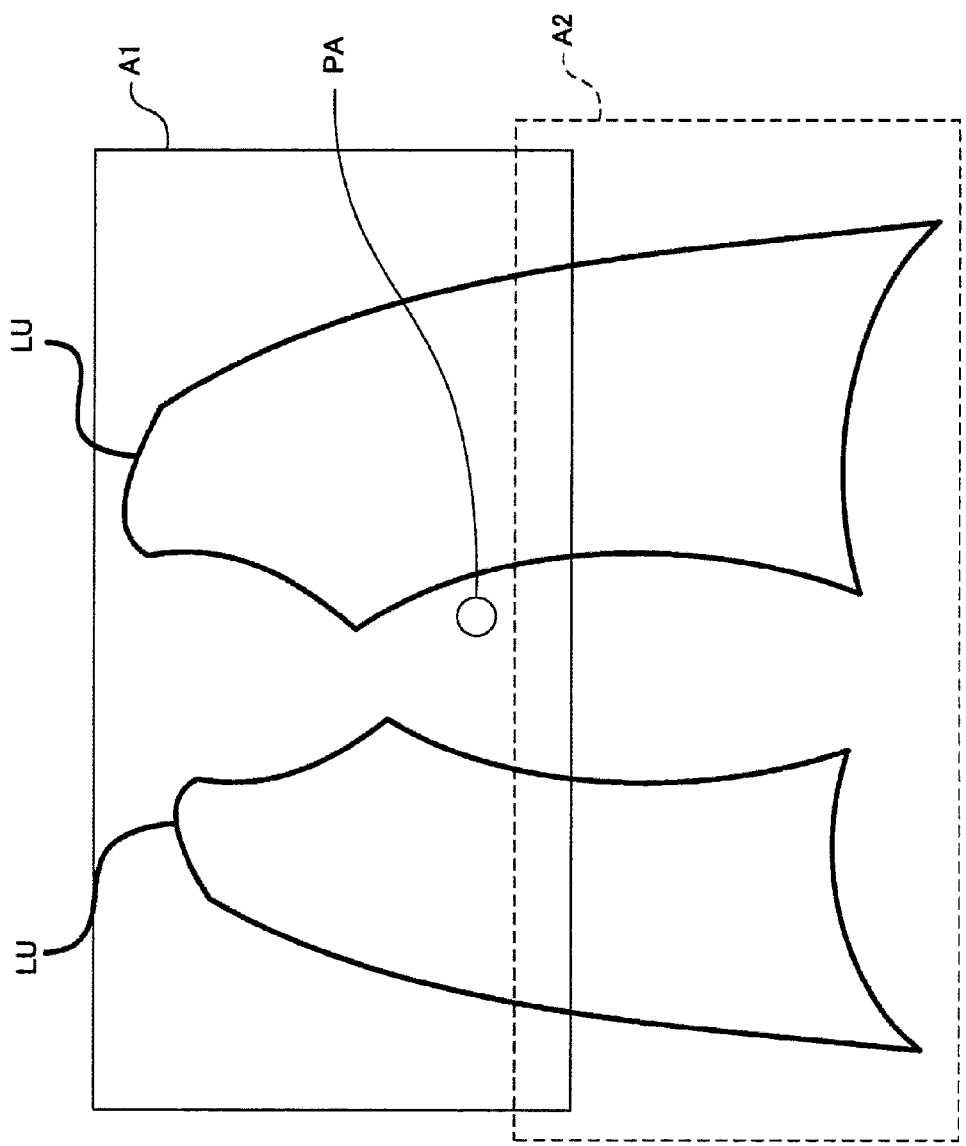
FIG. 7 is a schematic diagram illustrating the outline of the medical image analyzer of the embodiment.
Figure 8:
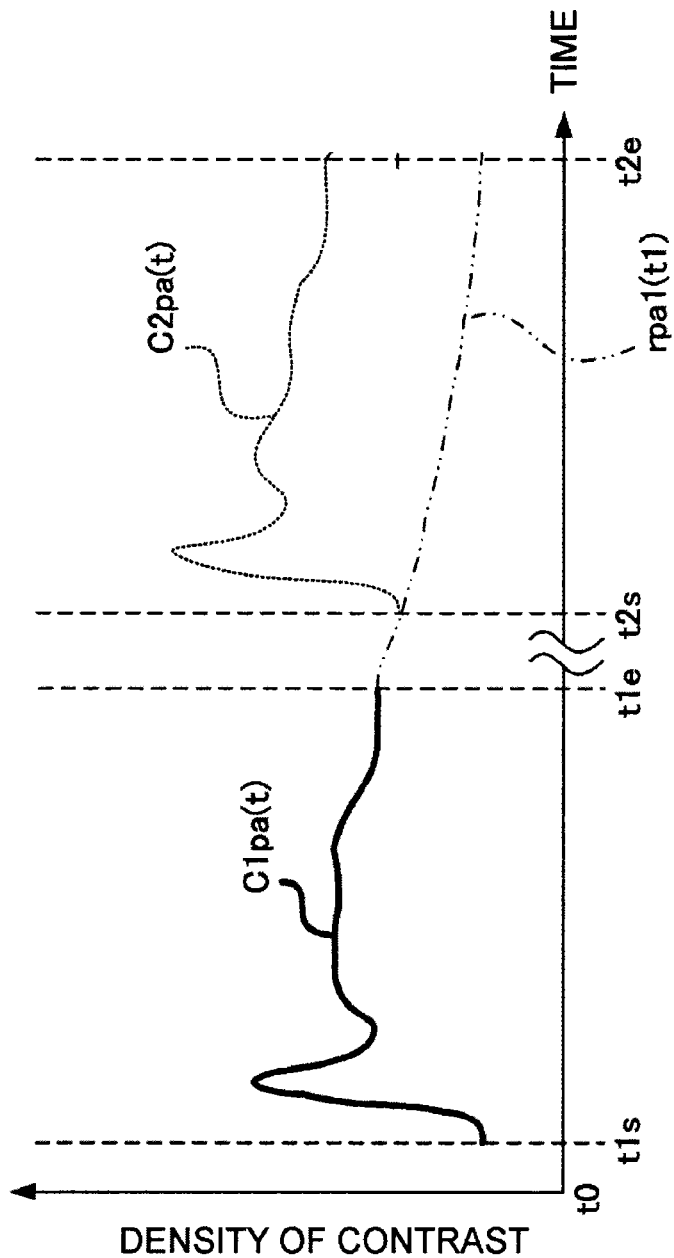
FIG. 8 is a schematic diagram illustrating the outline of the medical image analyzer of the embodiment.

FIG. 8 is a schematic diagram illustrating the time density curve obtained by the capturing as illustrated in FIG. 7. The horizontal axis represents time and the vertical axis represents pixel value. In FIG. 8, the time density curve C1pa(t) of the artery area PA of the pulmonary artery is obtained in a period from the capturing start time t1s to the capturing end time t1e of the first time-series image. the time density curve C2pa(t) of the artery area PA of the pulmonary artery is not obtained in a period from capturing start time t2s to the capturing end time t2e of the second time-series image. Described below is an example in which, in the example of FIG. 8, the medical image analyzer 1 of this embodiment obtains the second artery transition information in the second time-series image.

Having received the time-series images retrieved by the retriever 10 and the time-phase association information from the time-phase association unit 19, the tissue transition information unit 14 obtains tissues transition information that represents a time-series change in the pixel value in the tissue of the subject.

The tissue area extractor 20 extracts an image area that represents the tissue to be analyzed from each of the time-series images retrieved by the retriever 10. For example, the tissue area extractor 20 stores in advance shape data representing the shape of the tissue to be analyzed, and compares the shape of an image rendered in the time-series images with the shape data to extract the image area representing an analysis target. When the analysis target is the lungs LU, the tissue area extractor 20 extracts an image area representing the lungs LU from the time-series images. The tissue area extractor 20 outputs the image area thus extracted to the artery pixel information unit 21.

Having received the time-series images retrieved by the retriever 10, the time-phase association information obtained by the time-phase association unit 19, and the image area extracted by the tissue area extractor 20, the artery pixel information unit 21 obtains artery pixel transition information that represents the transition of the pixel value of each pixel in the image area. At this time, the artery pixel information unit 21 may perform gray-scale morphology processing or other general filtering on each of the time-series images and extract the shape of the tissue rendered in the image area more clearly to obtain the artery pixel transition information for each pixel. The artery pixel information unit 21 may perform gray-scale dilation when performing the gray-scale morphology processing on the time-series images.

The artery pixel information unit 21 extracts information related to a pixel corresponding to an artery pixel from the artery pixel transition information obtained. The artery pixel is a pixel representing an artery in the tissue to be analyzed, and is different from that in the artery area PO of the pulmonary artery specified. For example, the artery pixel information unit 21 stores in advance blood vessel classification information that represents the characteristics of each type of blood vessel. The blood vessel classification information represents, for example, the characteristics of the time density curve for each type of blood vessel such as the pulmonary artery and the bronchial artery, and is, in general, similar to the example illustrated in FIG. 3. Besides, regarding the pulmonary artery, it is known that peak height PH is large, curve width FW is small. The artery pixel information unit 21 stores a threshold for each of the peak height PH and the curve width FW as the blood vessel classification information. The artery pixel information unit 21 extracts a pixel with the peak height PH greater than the threshold and the curve width FW smaller than the threshold as a pixel representing the pulmonary artery. Thereby, pixels representing the pulmonary artery are extracted from the pixels in the image area where the lungs LU are rendered.

The artery pixel information unit 21 obtains transition information of the pixel value represented in the artery pixel transition information for a pixel in the overlapping area among the artery pixels extracted. For example, the artery pixel information unit 21 obtains artery pixel transition information C11_pa_i(t) (i=1 to N: N is the number of pulmonary artery pixels in the overlapping area between the first area A1 and the second area A2) for pulmonary artery pixels in an area of the first area A1 overlapping the second area A2. Since the registration has already been performed by the time-phase association unit 19 for frames of the time-series images, the artery pixel transition information can be regarded as information representing the transition of the concentration of a contrast agent in the same tissue. The artery pixel information unit 21 calculates the average of the artery pixel transition information obtained for the pulmonary artery pixels, and obtains transition information C11_pa(t) that represents the transition of the average value. Similarly, the artery pixel information unit 21 extracts pulmonary artery pixels in an area of the second area A2 overlapping the first area A1, and obtains transition information C2u_pa(t) that represents the transition of the average value of the artery pixels. The artery pixel information unit 21 outputs the transition information thus obtained to the second artery transition information unit 15. While, in the example described above, the artery pixel information unit 21 obtains transition information of artery pixels in the overlapping area, instead, it may obtain transition information of artery pixels in the entire image area extracted by the tissue area extractor 20. This can simplify the calculation process of the transition information.

The second artery transition information unit 15 obtains the transition information of the artery over the capturing time of all the time-series images as second artery transition information. The second artery transition information unit 15 corrects the time deviation between the contrast agent administration time and the capturing start time for each time-series image by, for example, the following equations:

$$T = t1e - t1s = t2e - t2s$$

$$t1 = t - s1 - t1s : t1s \leq t \leq t1e$$

$$t2 = t - s2 - t2s : t2s \leq t \leq t2e \qquad \text{[Equations 7]}$$

where t is the time that has elapsed from the reference time t0, s1 is the time deviation of the first time-series image, s2 is the time deviation of the second time-series image, t1s is the capturing start time of the first time-series image, t1e is the capturing end time of the first time-series image, t2s is the capturing start time of the second time-series image, and t2e is the capturing end time of the second time-series image.

In addition, the second artery transition information unit 15 represents the time density curve of the pulmonary artery in the overlapping area by, for example, the following equations:

$$C1l_{pa}(t) = a1 \times Dpa(t1) \qquad \text{[Equations 8]}$$

$$C2u_{pa}(t) = a1 \times rpa1(t) + a2 \times Dpa(t2)$$

$$rpa1(x) = Dpa(T)\exp\left(-\frac{x - t1e}{T1}\right); \ x > t1e$$

In Equations 8, $C1l_{pa}(t)$ represents the time density curve of the pulmonary artery in the overlapping area between the first area A1 and the second area A2 in the first time-series image. $C2u_{pa}(t)$ represents the time density curve of the pulmonary artery in the overlapping area between the first area A1 and the second area A2 in the second time-series image. The function value of rpa1(x) is assumed to be zero in the outside of the range of x. T1 is unknown. Besides, Dpa(t) is a time density curve for the pulmonary artery which does not include the influence of circulations after the secondary circulation, and is unknown. At this time, it may be possible that s1=0. In addition, a1, a2 and a3 are unknown, and are coefficients to be multiplied to the attenuation curve. Further, a1, a2 and a3 are coefficients to correct for partial volume effect. If there is no need to correct the partial volume effect, they may be in the following relationship: a1=a2=a3=1.

The second artery transition information unit 15 represents the time density curve of the pulmonary artery in the overlapping area between the first area A1 and the second area A2 of the second time-series image based on Equations 7 and 8 by, for example, the following equation:

$$C2u_{pa}(t) = C1l_{pa}(t1e) \times \exp\left(-\frac{x - t1e}{T1}\right) + \qquad \text{[Equation 9]}$$
$$\frac{a2}{a1} \times C1l_{pa}(t - t2s - s2 + t1s); \ t2s \leq t \leq t2e$$

The second artery transition information unit 15 represents the first artery transition information $C1_{pa}(t)$ by the following equation:

$$C1_{pa}(t) = Dpa(t1) \qquad \text{[Equation 10]}$$

The second artery transition information unit 15 represents the time density curve $C1l_{pa}(t)$ of the pulmonary artery in the overlapping area between the first area A1 and the second area A2 of the first time-series image based on Equations 8 and 10 by, for example, the following equation:

$$C1l_{pa}(t) = a1 \times C1pa(t) \qquad \text{[Equation 11]}$$

The second artery transition information unit 15 obtains the variables of a1, a2, s2 and T1 based on the system of equations consisting of equations selected from Equations 8, 9, 10 and 11. At this time, the second artery transition information unit 15 may use a general regularization method as appropriate. The second artery transition information unit 15 may also use general heuristics approach. Incidentally, when the system of equations is not required to include all equations selected from Equations 8, 9, 10 and 11, the second artery transition information unit 15 may select necessary equations for the system of equations.

Using the transition information C1pa(t) of the origin of the pulmonary artery received from the first artery transition information unit 11 and Equation 10, the second artery transition information unit 15 obtains the time density curve $D_{pa}(t)$ of the pulmonary artery which does not include the influence of circulations after the secondary circulation by the following equation:

$$D_{pa}(t)=C1pa(t+t1s) \quad \text{[Equation 12]}$$

The second artery transition information unit 15 represents transition information related to the artery area PA of the origin of the pulmonary artery over the capturing time of both the first time-series image and the second time-series image of by the following equation:

$$Cpa(t)=Dpa(t1)+rpa1(t)+Dpa(t2) \quad \text{[Equation 13]}$$

Further, the second artery transition information unit 15 represents transition information related to the artery area PA of the origin of the pulmonary artery with respect to times before and after the capturing end time t1e of the first time-series image based on Equation 13 by the following two equations:

$$Cpa(t) = C1pa(t) + C1pa(t - s2 - t2s + t1s): t \le t1e \quad \text{[Equation 14]}$$

$$Cpa(t) = C1pa(t) \times \exp\left(-\frac{x-t1e}{T1}\right) + \quad \text{[Equation 15]}$$
$$C1pa(t - s2 - t2s + t1s): t > t1e$$

The second artery transition information unit 15 substitutes s2 and T1 thus obtained into Equation 14. Thereby, it is possible to obtain transition information Cpa(t) related to the artery area PA of the pulmonary artery over the capturing time of both the first time-series image and the second time-series image. In the time range of Equation 15, transition information represented in a range from the capturing start time t2s until the capturing end time t2e corresponds to the artery transition information of the pulmonary artery for the second time-series image, and the transition can be considered as represented by the time density curve C2pa(t). The second artery transition information unit 15 outputs the transition information Cpa(t) thus obtained to the analyzer 16.

The analyzer 16 performs perfusion analysis on each of the time-series images according to a specified analysis method based on the first artery transition information obtained by the first artery transition information unit 11, the second artery transition information obtained by the second artery transition information unit 15, and the tissue transition information obtained by the tissue transition information unit 14. At this time, the analyzer 16 performs perfusion analysis using transition information represented in a time range from the capturing start time t1s until the capturing end time t1e in the transition information Cpa(t) received from the second artery transition information unit 15 as the input function of the first time-series image. In addition, the analyzer 16 performs perfusion analysis using transition information represented in a time range from the capturing start time t2s until the capturing end time t2e in the transition information Cpa(t) received from the second artery transition information unit 15 as the input function of the second time-series image. The analyzer 16 performs perfusion analysis with respect to each pixel of the time-series images. The analyzer 16 feeds the image generator 17 with the blood flow dynamics, such as the blood-flow volume or blood volume of the tissue of the subject represented by each pixel, as an analysis result.

In this embodiment, an example is described in which the pulmonary artery area PA, which represents the origin of the pulmonary artery, is specified in the first area A1 and outside the second area A2. When the artery area of the aorta is specified in the first area A1 and outside the second area A2, second artery transition information of the aorta in the second time-series image may be obtained in a similar manner.

Besides, the artery area PA of the pulmonary artery or the artery area of the aorta may be specified any one of the plurality of areas. With the above configuration, the medical image analyzer 1 may obtain the second artery transition information for another area that overlaps the area where the artery area PA of the pulmonary artery or the artery area of the aorta is specified. Further, an example is described above in which the lungs LU2 are divided into two areas to capture a medical image thereof by capturing the two areas. When the medical image is captured by capturing three or more areas, the medical image analyzer 1 may sequentially obtain the second artery transition information for an area that overlaps the area where an artery area is specified.

Figure 9:
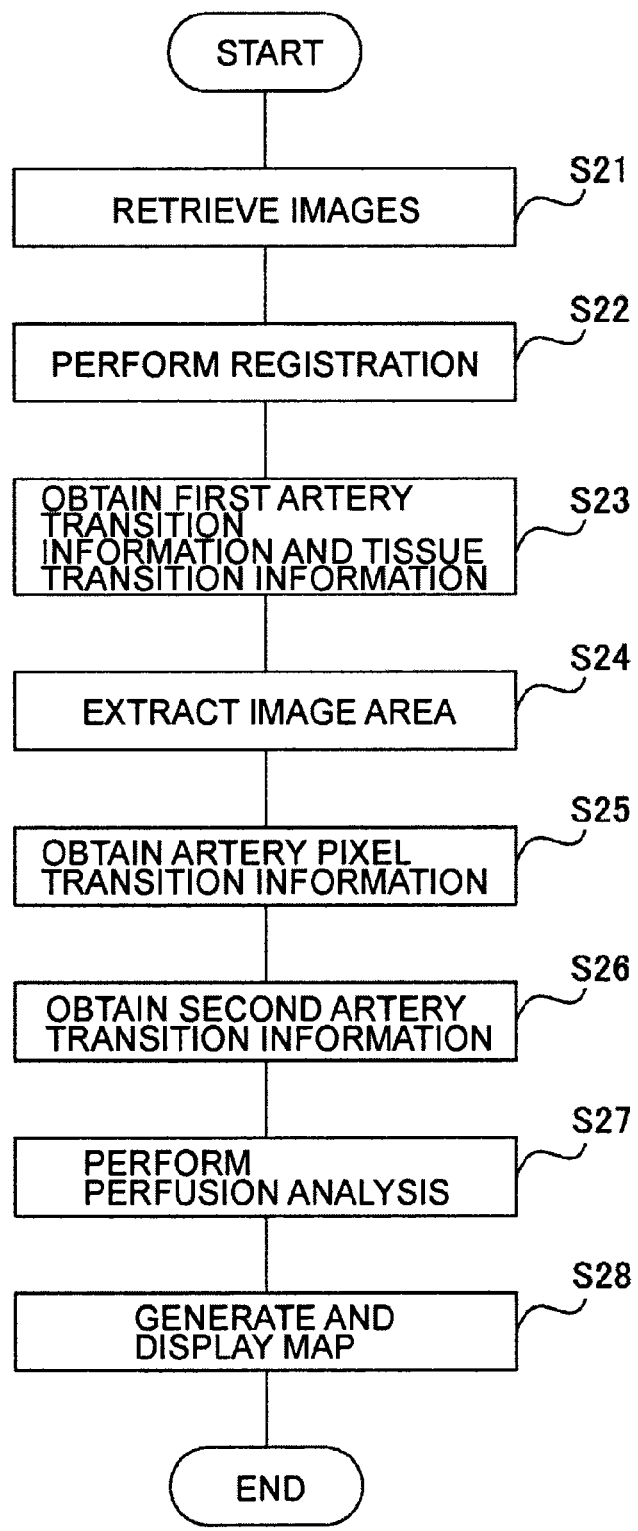
FIG. 9 is a flowchart of an example of the operation of the medical image analyzer of the embodiment.

Described below is the operation of the medical image analyzer 1 of this embodiment. FIG. 9 is a flowchart illustrating the operation of this embodiment.

S21: The retriever 10 retrieves, from the storage 2, a plurality of time-series images captured of a plurality of areas of a subject having been administered a contrast agent at different times such that the images have an overlapping area.

S22: The time-phase association unit 19 performs registration between pixels in frames of the time-series images retrieved by the retriever 10.

S23: The first artery transition information unit 11 obtains first artery transition information that represents the transition of the pixel value in an artery area based on the artery area specified in a part of the time-series images retrieved by the retriever 10. Besides, having received the time-series images retrieved by the retriever 10, the tissue transition information unit 14 obtains tissue transition information that represents a time-series change in the pixel value in the tissue of the subject.

S24: The tissue area extractor 20 extracts an image area that represents the tissue to be analyzed from each of the time-series images retrieved by the retriever 10. The tissue area extractor 20 outputs the image area thus extracted to the artery pixel information unit 21.

S25: Having received the time-series images retrieved by the retriever 10, the time-phase association information obtained by the time-phase association unit 19, and the image area extracted by the tissue area extractor 20, the artery pixel information unit 21 obtains artery pixel transition information that represents the transition of the pixel value of each pixel in the image area. The artery pixel information unit 21 outputs the transition information thus obtained to the second artery transition information unit 15.

S26: The second artery transition information unit 15 obtains the transition information of the artery area over the capturing time of all the time-series images as second artery transition information. The second artery transition information unit 15 outputs the transition information thus obtained to the analyzer 16.

S27: The analyzer 16 performs perfusion analysis on each of the time-series images according to a specified analysis method based on the second artery transition information obtained by the second artery transition information unit 15, and the tissue transition information obtained by the tissue transition information unit 14.

S28: Having received the time-series images registered to each other by the image association unit 13 and the analysis result from the analyzer 16, the image generator 17 generates a map that represents the hemodynamics of the tissue of the subject. The image generator 17 displays the map on the display 4.

According to the second embodiment, the medical image analyzer 1 includes the time-phase association unit 19, the first artery transition information unit 11, the tissue area extractor 20, the artery pixel information unit 21, and the second artery transition information unit 15. The time-phase association unit 19 is configured to perform registration between pixels in frames of the time-series images. The first artery transition information unit 11 is configured to obtain first artery transition information that represents a transition of pixel value in an artery area based on the artery area specified in a part of the time-series images. The tissue area extractor 20 is configured to extract an image area that represents tissue to be analyzed from each of the time-series images. The artery pixel information unit 21 is configured to receive the time-series images, the time-phase association information, and the image area, and obtain artery pixel transition information that represents a transition of pixel value of each pixel in the image area. The second artery transition information unit 15 is configured to obtain transition information of the artery area over capturing time of all the time-series images as second artery transition information. Thereby, the medical image analyzer 1 obtains an input function for the time-series images where an artery area is not specified based on transition information of the pixel value in the artery area specified in any one of the areas. Thus, the medical image analyzer 1 can perform perfusion analysis on the time-series images.

Third Embodiment

Figure 10:
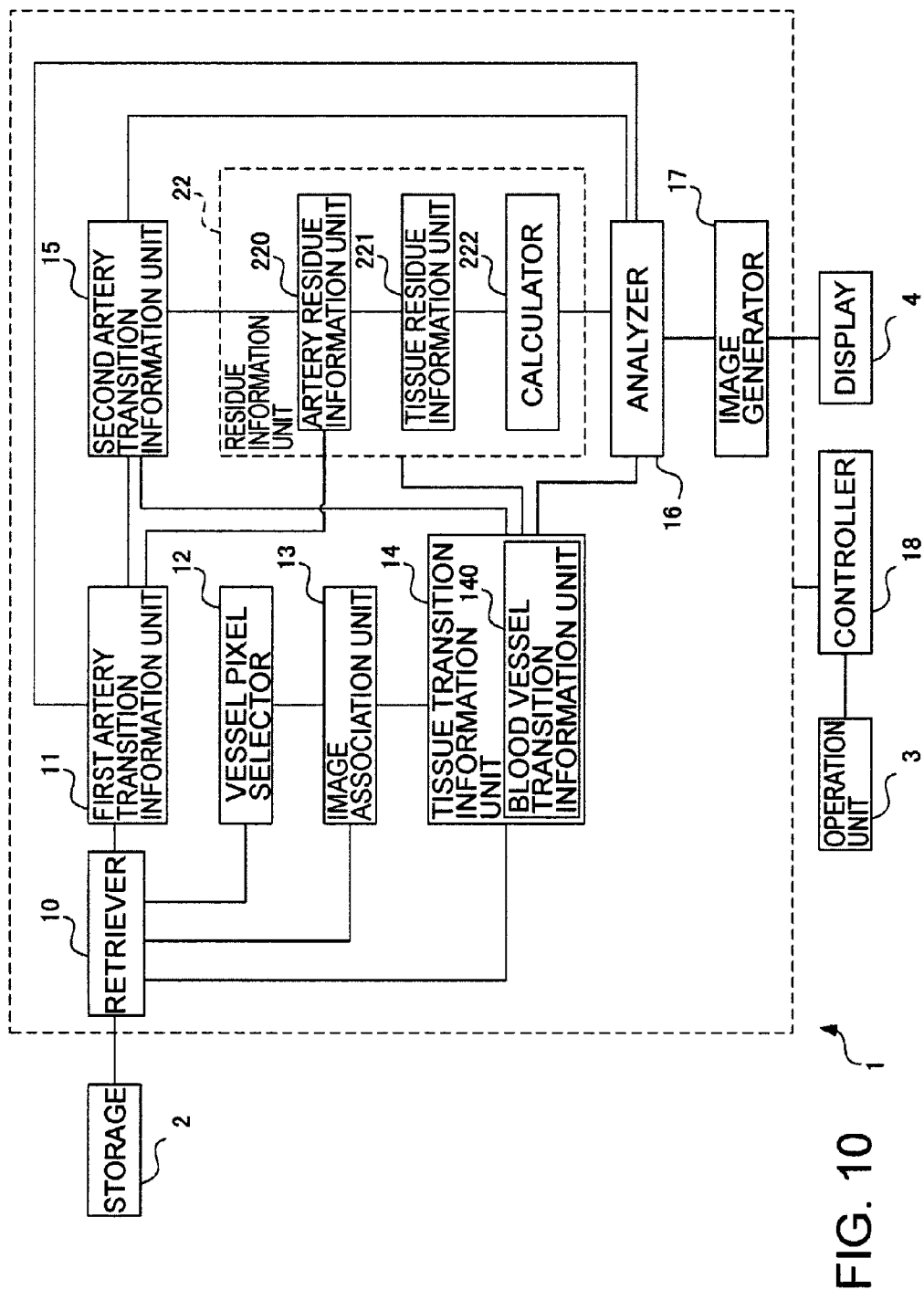
FIG. 10 is a functional block diagram illustrating an example of the configuration of a medical image analyzer according to still another embodiment.

With reference to FIG. 10, a description is given of the configuration of the medical image analyzer 1 according to the third embodiment. The medical image analyzer 1 of this embodiment differs from that of the first embodiment in a residue information unit 22. In the following, the differences from the first embodiment are mainly described.

The residue information unit 22 reduces the effect of residual contrast agent for the transition information of the pixel value of each pixel in the time-series images.

An artery residue information unit 220 obtains, with respect to each of the time-series images, artery residue information that represents the transition of the pixel value due to a contrast agent administered for capturing a previous time-series image before the capturing of the current one based on either or both of the first artery transition information obtained by the first artery transition information unit 11 and the second artery transition information obtained by the second artery transition information unit 15. Here, the artery residue information unit 220 obtains the artery transition information when the administration of contrast agent is stopped at a certain number of times of administration based on information that has become known from Equations 1 to 6 by, for example, the following equations:

$$E1pa(t)=Dpa(t1)+rpa1(t2)$$

$$E1ao(t)=Dba(t1)+rba1(t2)$$

$$E2pa(t)=rpa1(t1)+Dpa(t2)+rpa2(t2)$$

$$E2ao(t)=rba1(t1)+Dba(t2)+rba2(t2) \quad \text{[Equations 16]}$$

In Equations 16, E1pa(t) is artery transition information of the pulmonary artery when a contrast agent is administered once (the administration of a contrast agent for the first time-series image) without the second and subsequent administration. E1ao(t) is artery transition information of the aorta when a contrast agent is administered once without the second and subsequent administration. E1pa(t) is artery transition information of the pulmonary artery when a contrast agent is administered twice (the administration of a contrast agent for the first and second time-series images) without the third and subsequent administration. E2ao(t) is artery transition information of the aorta when a contrast agent is administered twice without the third and subsequent administration. The artery residue information unit 220 obtains artery transition information about a contrast agent administered before the capturing time of each of the second and third time-series images by, for example, Equations 17:

$$E1pa(x)=rpa1(x):t2s \leq x \leq t2e$$

$$E1ao(x)=rba1(x):t2s \leq x \leq t2e$$

$$E2pa(x)=rpa2(x):t3s \leq x \leq t3e$$

$$E2ao(x)=rpa2(x):t3s \leq x \leq t3e \quad \text{[Equations 17]}$$

In Equations 17, E1pa(x) is transition information in the capturing time of the second time-series image in E1pa(t) of Equations 16. In other words, E1pa(x) is the estimate of the transition of the concentration of a contrast agent administered first on the pulmonary artery in the capturing time of the second time-series image. E1ao(x) is transition information in the capturing time of the second time-series image in E1ao(t) of Equations 16. In other words, E1ao(x) is the estimate of the transition of the concentration of a contrast agent administered first on the aorta in the capturing time of the second time-series image. E2pa(x) is transition information in the capturing time of the third time-series image in E2pa(t) of Equations 16. In other words, E2pa(x) is the estimate of the transition of the concentration of a contrast agent administered on the pulmonary artery up to the second time in the capturing time of the third time-series image. E2ao(x) is transition information in the capturing time of the third time-series image in E2ao(t) of Equations 16. In other words, E2ao(x) is the estimate of the transition of the concentration of a contrast agent administered on the aorta up to the second time in the capturing time of the third time-series image. E1pa(x), E1ao(x), E2pa(x), and E2ao(x) correspond to the artery residue information in this embodiment.

A tissue residue information unit 221 obtains tissue residue information that represents the transition of the pixel value based on the artery residue information obtained by the artery residue information unit 220 with respect to each pixel of the time-series images. The tissue residue information unit 221 performs model fitting using an imaging model specified by either or both of the first artery transition information obtained by the first artery transition information unit 11 and the second artery transition information obtained by the second artery transition information unit 15, the artery residue information, and the tissue transition information obtained by the tissue transition information unit 14 to obtain parameters related to the imaging model. The tissue residue information unit 221 then obtains the tissue residue information based on the artery residue information, the imaging model, and the parameters thus obtained. At this time, the tissue residue information unit 221 obtains, as a parameter, the damping time constant representing the attenuation of the pixel value of each pixel in the time-series images. For example, the tissue residue information unit 221 performs model fitting using an imaging model of the following equation:

$$C(t)=Ca(t)*\alpha \exp(-t/\beta) \quad \text{[Equation 18]}$$

In Equation 18, transition information Cpa(t), Cba(t) obtained by Equations 6 or transition information obtained by weighted addition of them is used as Ca(t). Here, Cpa(t) and Cba(t) include either or both of the first artery transition information obtained by the first artery transition information unit 11 and the second artery transition information obtained by the second artery transition information unit 15. The tissue transition information obtained by the tissue transition information unit 14 is used as C(t). Besides, * represents a convolution integral. In addition, α and β are parameters related to the imaging model. Further, β is a damping time constant representing the attenuation of the pixel value of each pixel in the time-series images. Incidentally, the tissue residue information unit 221 may use an imaging model of the following equations:

$$C(t)=\alpha Ca(t)*R(t,\beta)$$

$$C(t)=\alpha Ca(t)*R(t,a,b,c)*\exp(-t/\beta) \quad \text{[Equations 19]}$$

In Equations 19, R(t, β) and R(t, a, b, c) represent residual functions. Each of α, β, a, b and c is a parameter related to the imaging model. Further, β is a damping time constant representing the attenuation of the pixel value of each pixel in the time-series images. The user may specify the imaging model using the operation unit 3, or it may be preset in the tissue residue information unit 221. In this embodiment, an example is described in which the tissue residue information unit 221 uses the imaging model of Equation 18.

The tissue residue information unit 221 performs model fitting by fitting the imaging model of Equation 18 to the tissue transition information of each pixel of the time-series images. At this time, for example, the tissue residue information unit 221 obtains parameters α and β related to the imaging model using an optimization method. Then, the tissue residue information unit 221 obtains the tissue residue information based on the artery residue information of Equations 17, the imaging model of Equation 18, and the parameters α and β obtained by, for example, the following equations:

$$G2(t)=E1(t)*\alpha \exp(-t/\beta)$$

$$G3(t)=E2(t)*\alpha \exp(-t/\beta) \quad \text{[Equations 20]}$$

In Equations 20, E1pa(x), E1ao(x) obtained as artery residue information by Equations 17, or transition information obtained by weighted addition of them is used as E1(t). E2pa(x), E2ao(x) obtained as artery residue information by Equations 17, or transition information obtained by weighted addition of them is used as E2(t). G2(t) represents tissue transition information in response to the artery transition information of a contrast agent administered for the first time in the capturing time of the second time-series image. G3(t) represents tissue transition information in response to the artery transition information of a contrast agent administered up to the second time in the capturing time of the third time-series image. The tissue residue information unit 221 obtains G2(t) as the tissue residue information in the second time-series image, and G3(t) as the tissue residue information in the third time-series image.

A calculator 222 subtracts the pixel value G2(t), G3(t) represented by the tissue residue information obtained by the tissue residue information unit 221 from the pixel value C(t) represented by the tissue transition information obtained by the tissue transition information unit 14, for example, as follows:

$$C'2(t)=C(t)-G2(t)$$

$$C'3(t)=C(t)-G3(t) \quad \text{[Equations 21]}$$

In Equations 21, C'2(t) represents tissue transition information obtained by correcting the effect of the contrast agent administered first for the tissue transition information of the second time-series image. C'3(t) represents tissue transition information obtained by correcting the effect of the contrast agent administered up to the second time for the tissue transition information of the third time-series image. The calculator 222 sends the tissue transition information C'2(t) and C'3(t) as corrected information to the analyzer 16.

The analyzer 16 performs perfusion analysis on each of the time-series images according to a specified analysis method based on the first artery transition information obtained by the first artery transition information unit 11, the second artery transition information obtained by the second artery transition information unit 15, the tissue transition information obtained by the tissue transition information unit 14, and the tissue transition information corrected by the calculator 222. For example, the analyzer 16 performs perfusion analysis on the tissue transition information obtained by the tissue transition information unit 14 according to the specified analysis method using C1pa(t) and C1ao(t) as input functions in the first time-series image. Further, the analyzer 16 performs perfusion analysis on the tissue transition information C'2(t) corrected by the calculator 222 using C2pa(t) and C2ao(t) as input functions in the second time-series image. The analyzer 16 also performs perfusion analysis on the tissue transition information C'3(t) corrected by the calculator 222 using C3pa(t) and C3ao(t) as input functions for the third time-series image. In other words, the analyzer 16 performs perfusion analysis on the tissue transition information corrected by the calculator 222 in the second and third time-series images captured by the second and subsequent photography among the time-series images. Thereby, the analyzer 16 performs perfusion analysis using the tissue residue information as a baseline in the second time-series image and the third time-series image.

Figure 11:
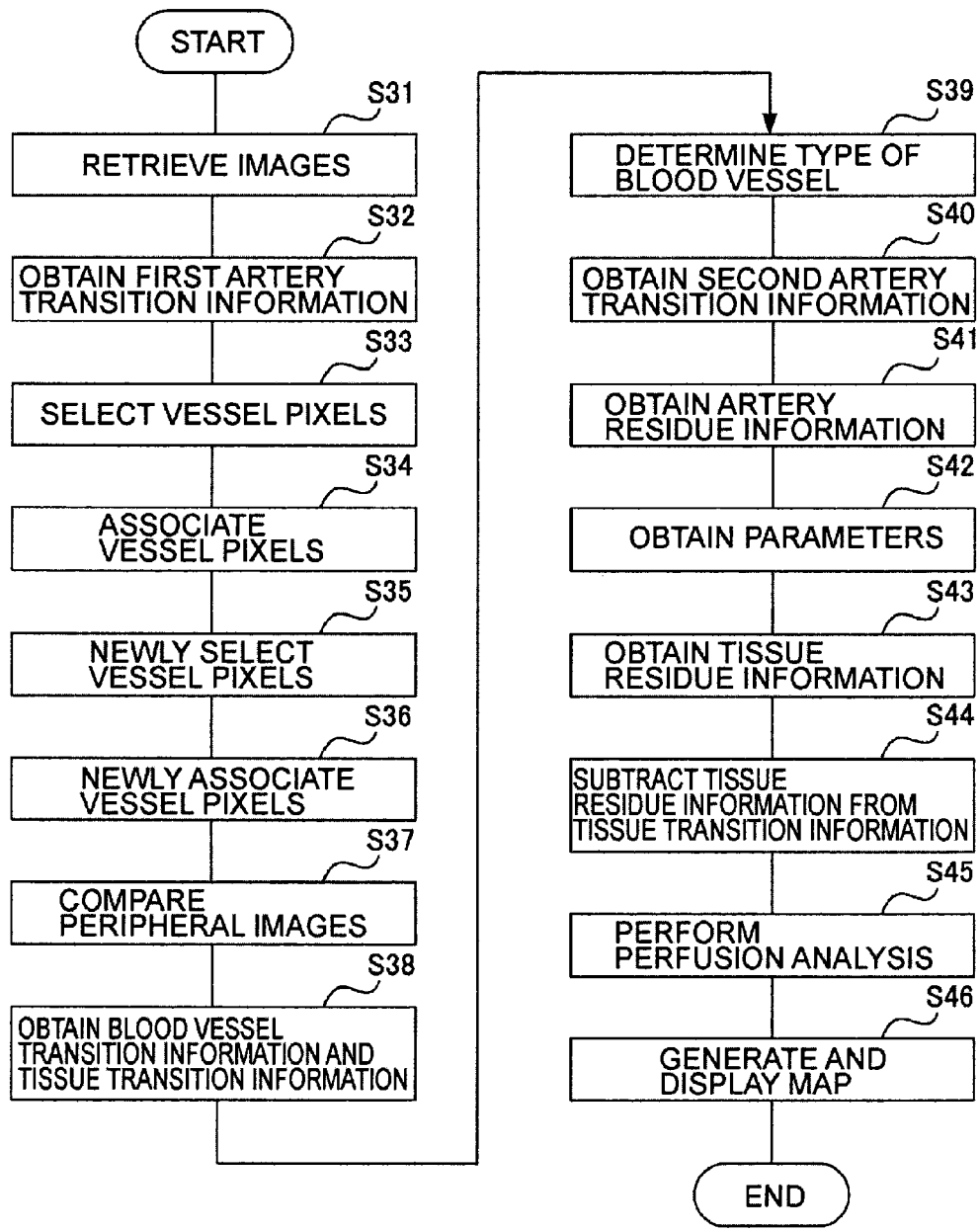
FIG. 11 is a flowchart of an example of the operation of the medical image analyzer of the embodiment.

Described below is the operation of the medical image analyzer 1 of this embodiment. FIG. 11 is a flowchart illustrating the operation of this embodiment.

S31: The retriever 10 retrieves, from the storage 2, a plurality of time-series images captured of a plurality of areas of a subject having been administered a contrast agent at different times such that the images have an overlapping area. The retriever 10 further retrieves, from the storage 2, an entire area image representing all the areas of the subject that has not been administered a contrast agent.

S32: The first artery transition information unit 11 obtains first artery transition information that represents the transition of the pixel value in an artery area based on the artery area specified in a part of the time-series images retrieved by the retriever 10.

S33: The vessel pixel selector 12 selects vessel pixels each representing a blood vessel from the pixels of the time-series images retrieved by the retriever 10. The vessel pixel selector 12 also selects an entire area vessel pixel representing a blood vessel from the pixels of the entire area image retrieved by the retriever 10.

S34: The image association unit 13 associates the vessel pixels with the entire area vessel pixel selected by the vessel pixel selector 12. Thereby, a vessel pixel in an overlapping area in one of the time-series images is associated with a vessel pixel in the overlapping area in another time-series image. The image association unit 13 specifies an area corresponding to the overlapping area in the entire area image.

S35: The vessel pixel selector 12 newly selects first overlapping area vessel pixels each representing a blood vessel from among pixels of the area corresponding to the overlapping area in the entire area image specified by the image association unit 13 at a higher density than the entire area vessel pixel associated therewith by the image association unit 13. In addition, the vessel pixel selector 12 newly selects second overlapping area vessel pixels each representing a blood vessel from among pixels in the overlapping area of the time-series images at a higher density than the vessel pixels.

S36: The image association unit 13 associates a part of the first overlapping area vessel pixels with a part of the second overlapping area vessel pixels. Thereby, the vessel pixel in the overlapping area in one of the time-series images is associated with the vessel pixel in the overlapping area in another time-series image.

S37: The image association unit 13 compares a first peripheral image with a second peripheral image. The first peripheral image is an image of an area including first unassociated pixels, i.e., pixels in the first overlapping area vessel pixels, which are not associated with the second overlapping area vessel pixels. The second peripheral image is an image of an area including second unassociated pixels, i.e., pixels corresponding to a peripheral image in the time-series images. When the degree of coincidence between the first peripheral image and the second peripheral image exceeds a specified value, the image association unit 13 further associates the first unassociated pixels and the second unassociated pixels.

S38: The blood vessel transition information unit 140 obtains blood vessel transition information that represents the transition of the pixel value of the vessel pixels associated by the image association unit 13. Besides, having received the time-series images retrieved by the retriever 10, the tissue transition information unit 14 obtains tissue transition information that represents a time-series change in the pixel value in the tissue of the subject.

S39: The second artery transition information unit 15 stores in advance blood vessel classification information that represents the characteristics of each type of blood vessel. The second artery transition information unit 15 determines the type of the blood vessel represented by the vessel pixels associated by the image association unit 13 based on the blood vessel transition information obtained by the blood vessel transition information unit 140 and the blood vessel classification information.

S40: The second artery transition information unit 15 obtains second artery transition information based on time information indicating the time of capturing each of the time-series images, the first artery transition information obtained by the first artery transition information unit 11, the blood vessel transition information obtained by the blood vessel transition information unit 140, and the correspondence relationship obtained by the image association unit 13. The second artery transition information corresponds to an artery area at the time of capturing time-series images other than those where the artery area is set.

S41: The artery residue information unit 220 obtains, with respect to each of the time-series images, artery residue information that represents the transition of the pixel value due to a contrast agent administered for capturing a previous time-series image before the capturing of the current one based on either or both of the first artery transition information obtained by the first artery transition information unit 11 and the second artery transition information obtained by the second artery transition information unit 15.

S42: The tissue residue information unit 221 performs model fitting using an imaging model specified by either or both of the first artery transition information obtained by the first artery transition information unit 11 and the second artery transition information obtained by the second artery transition information unit 15, the artery residue information, and the tissue transition information obtained by the tissue transition information unit 14 to obtain parameters related to the imaging model.

S43: The tissue residue information unit 221 obtains tissue residue information based on the artery residue information, the imaging model, and the parameters obtained.

S44: The calculator 222 subtracts the pixel value represented by the tissue residue information obtained by the tissue residue information unit 221 from the pixel value represented by the tissue transition information obtained by the tissue transition information unit 14.

S45: The analyzer 16 performs perfusion analysis on each of the time-series images according to a specified analysis method based on the first artery transition information obtained by the first artery transition information unit 11, the second artery transition information obtained by the second artery transition information unit 15, the tissue transition information obtained by the tissue transition information unit 14, and the tissue transition information corrected by the calculator 222.

S46: Having received the time-series images registered to each other by the image association unit 13 and the analysis result from the analyzer 16, the image generator 17 generates a map that represents the hemodynamics of the tissue of the subject. The image generator 17 displays the map on the display 4.

According to the third embodiment, the medical image analyzer 1 includes the artery residue information unit 220, the tissue transition information unit 14, the tissue residue information unit 221, and the calculator 222. The artery residue information unit 220 is configured to obtain, with respect to each of the time-series images, artery residue information that represents a transition of pixel value due to a contrast agent administered for capturing a previous time-series image before the capturing of the time-series image based on either or both of the first artery transition information and the second artery transition information. The tissue transition information unit 14 is configured to obtain tissue transition information that represents a transition of pixel value of each pixel in the time-series images. The tissue residue information unit 221 is configured to obtain tissue residue information that represents a transition of pixel value based on the artery residue information with respect to each pixel of the time-series images. The calculator 222 is configured to subtract the pixel value represented by the tissue residue information from the pixel value represented by the tissue transition information. In this manner, the medical image analyzer 1 obtains the effect of the contrast agent administered in the past as the tissue residue information. The medical image analyzer 1 performs perfusion analysis on transition information obtained by subtracting the tissue residue information from the tissue transition information, i.e., corrected tissue transition information. Thus, the medical image analyzer 1 can perform perfusion analysis on images of a subject having been administered a contrast agent a plurality of times captured by moving the imaging area with less effect of residual contrast agent.

Fourth Embodiment

Figure 12:
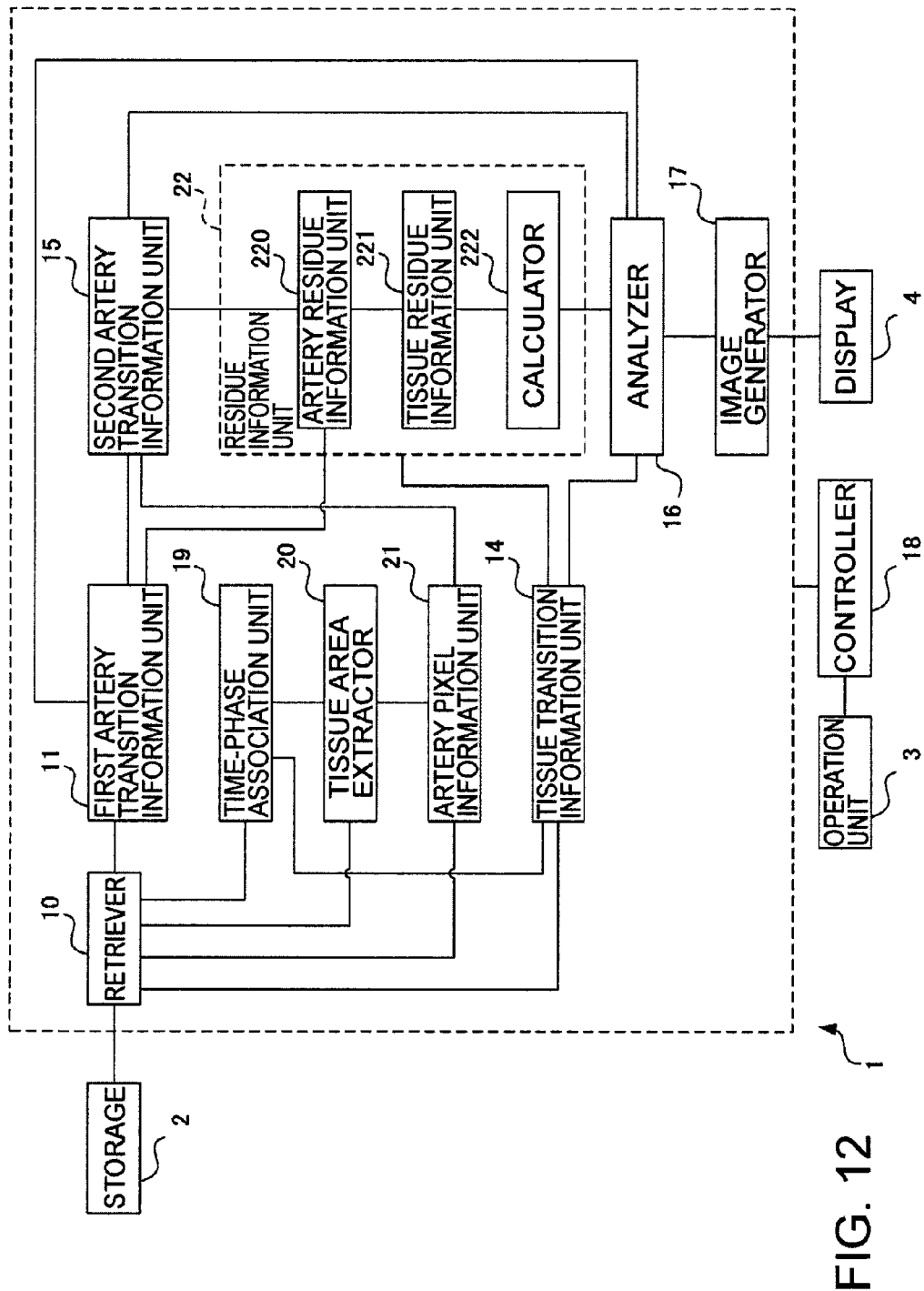
FIG. 12 is a functional block diagram illustrating an example of the configuration of a medical image analyzer according to still another embodiment.

FIG. 12 is a block diagram illustrating the configuration of the medical image analyzer 1 according to a fourth embodiment. The medical image analyzer 1 of this embodiment is basically similar in configuration to that of the second embodiment except the presence of the artery residue information unit 220, the tissue residue information unit 221, and the calculator 222 described in the third embodiment. The constituent elements function in the same manner as in the second and third embodiments.

Figure 13:
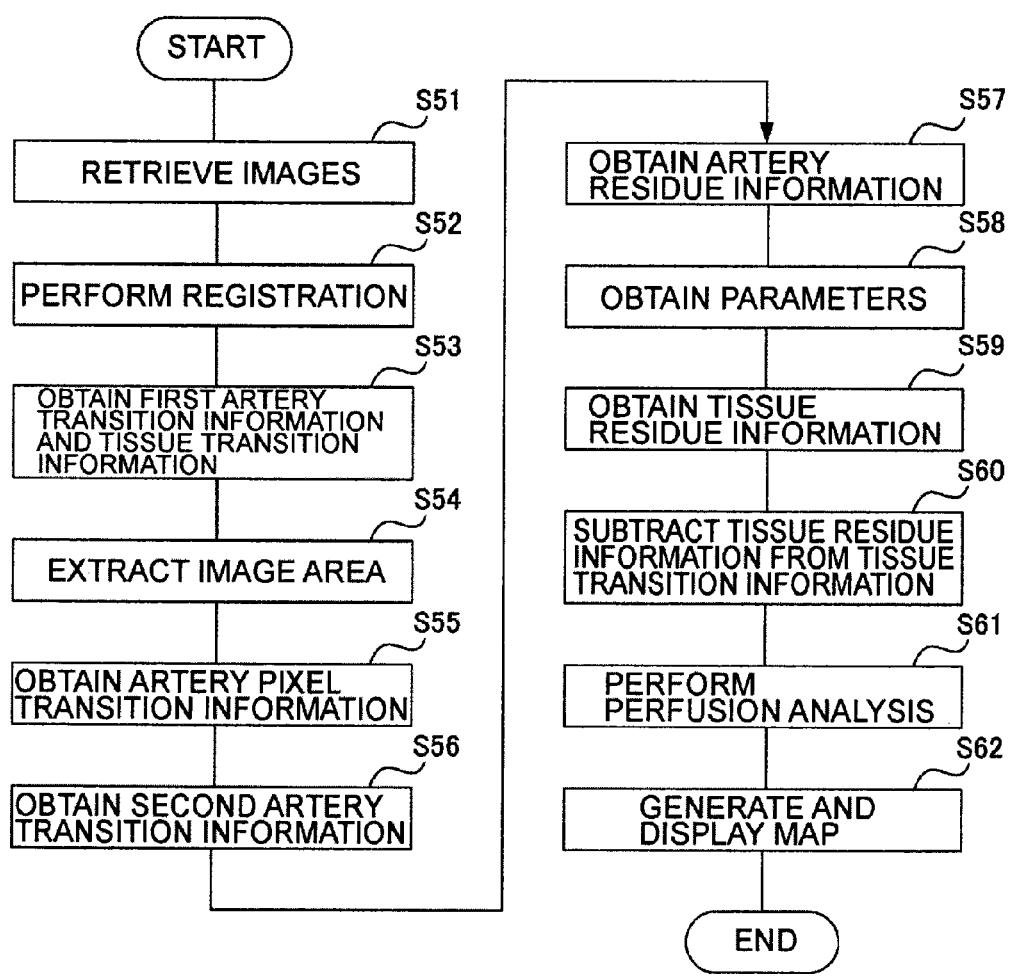
FIG. 13 is a flowchart of an example of the operation of the medical image analyzer of the embodiment.

Described below is the operation of the medical image analyzer 1 of this embodiment. FIG. 13 is a flowchart illustrating the operation of this embodiment.

S51: The retriever 10 retrieves, from the storage 2, a plurality of time-series images captured of a plurality of areas of a subject having been administered a contrast agent at different times such that the images have an overlapping area.

S52: The time-phase association unit 19 performs registration between pixels in frames of the time-series images retrieved by the retriever 10.

S53: The first artery transition information unit 11 obtains first artery transition information that represents the transition of the pixel value in an artery area based on the artery area specified in a part of the time-series images retrieved by the retriever 10. Besides, having received the time-series images retrieved by the retriever 10, the tissue transition information unit 14 obtains tissue transition information that represents a time-series change in the pixel value in the tissue of the subject.

S54: The tissue area extractor 20 extracts an image area that represents the tissue to be analyzed from each of the time-series images retrieved by the retriever 10. The tissue area extractor 20 outputs the image area thus extracted to the artery pixel information unit 21.

S55: Having received the time-series images retrieved by the retriever 10, the time-phase association information obtained by the time-phase association unit 19, and the image area extracted by the tissue area extractor 20, the artery pixel information unit 21 obtains artery pixel transition information that represents the transition of the pixel value of each pixel in the image area. The artery pixel information unit 21 outputs the transition information thus obtained to the second artery transition information unit 15.

S56: The second artery transition information unit 15 obtains the transition information of the artery area over the capturing time of all the time-series images as second artery transition information. The second artery transition information unit 15 outputs the transition information thus obtained to the analyzer 16.

S57: The artery residue information unit 220 obtains, with respect to each of the time-series images, artery residue information that represents the transition of the pixel value due to a contrast agent administered for capturing a previous time-series image before the capturing of the current one based on either or both of the first artery transition information obtained by the first artery transition information unit 11 and the second artery transition information obtained by the second artery transition information unit 15.

S58: The tissue residue information unit 221 performs model fitting using an imaging model specified by either or both of the first artery transition information obtained by the first artery transition information unit 11 and the second artery transition information obtained by the second artery transition information unit 15, the artery residue information, and the tissue transition information obtained by the tissue transition information unit 14 to obtain parameters related to the imaging model.

S59: The tissue residue information unit 221 obtains tissue residue information based on the artery residue information, the imaging model, and the parameters obtained.

S60: The calculator 222 subtracts the pixel value represented by the tissue residue information obtained by the tissue residue information unit 221 from the pixel value represented by the tissue transition information obtained by the tissue transition information unit 14.

S61: The analyzer 16 performs perfusion analysis on each of the time-series images according to a specified analysis method based on the first artery transition information obtained by the first artery transition information unit 11, the second artery transition information obtained by the second artery transition information unit 15, the tissue transition information obtained by the tissue transition information unit 14, and the tissue transition information corrected by the calculator 222.

S62: Having received the time-series images registered to each other by the image association unit 13 and the analysis result from the analyzer 16, the image generator 17 generates a map that represents the hemodynamics of the tissue of the subject. The image generator 17 displays the map on the display 4.

According to the fourth embodiment, the medical image analyzer 1 obtains the effect of the contrast agent administered in the past as the tissue residue information. The medical image analyzer 1 performs perfusion analysis on transition information obtained by subtracting the tissue residue information from the tissue transition information, i.e., corrected tissue transition information. Thus, the medical image analyzer 1 can perform perfusion analysis on images of a subject having been administered a contrast agent a plurality of times captured by moving the imaging area with less effect of residual contrast agent.

While an example is described above in which perfusion analysis is applied to the lungs, the embodiments are not limited to this. The perfusion analysis may be applied to the brain, heart, kidney, liver, and other tissues.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image analyzer configured to analyze time-series images of a subject to obtain hemodynamics of the subject, the medical image analyzer comprising processing circuitry configured to:
retrieve a plurality of time-series images captured of a plurality of areas of a subject having been administered a contrast agent at different times;
obtain first artery transition information that represents a transition of pixel value in an artery area based on the artery area specified in a part of the time-series images;

select vessel pixels each representing a blood vessel from pixels of the time-series images;

obtain blood vessel transition information that represents a transition of pixel value of the vessel pixels selected;

obtain a correspondence relationship between one and another of the time-series images; and obtain second artery transition information corresponding to the artery area at a time of capturing time-series images other than the part of the time-series images based on time information indicating a time of capturing each of the time-series images, the first artery transition information, the blood vessel transition information, and the correspondence relationship.

2. The medical image analyzer of claim 1, wherein the time-series images are captured to have an overlapping area, and the processing circuitry is further configured to associate, among the vessel pixels selected, a vessel pixel in the overlapping area in one of the time-series images with a vessel pixel in the overlapping area in another as having the correspondence relationship, and obtain a transition of pixel value of the vessel pixels as the blood vessels associated transition information.

3. The medical image analyzer of claim 2, wherein the processing circuitry is further configured to retrieve an entire area image representing all the areas of the subject that has not been administered the contrast agent, select an entire area vessel pixel that represents a blood vessel from among pixels of the entire area image, and associate the vessel pixels selected with the entire area vessel pixel to associate the vessel pixel in the overlapping area in the one of the time-series images with the vessel pixel in the overlapping area in the other as having the correspondence relationship.

4. The medical image analyzer of claim 3, wherein the processing circuitry is further configured to associate the vessel pixels selected with the entire area vessel pixel to associate the vessel pixel in the overlapping area in the one of the time-series images with the vessel pixel in the overlapping area in the other, and specify an area corresponding to the overlapping area in the entire area image, newly select first overlapping area vessel pixels each representing a blood vessel from among pixels of the area corresponding to the overlapping area specified at a higher density than the entire area vessel pixel, newly select second overlapping area vessel pixels each representing a blood vessel from among pixels in the overlapping area of the time-series images at a higher density than the vessel pixels, and associate a part of the first overlapping area vessel pixels with a part of the second overlapping area vessel pixels to associate the vessel pixel in the overlapping area in the one of the time-series images with the vessel pixel in the overlapping area in the other as having the correspondence relationship.

5. The medical image analyzer of claim 4, wherein the processing circuitry is further configured to when associating the part of the first overlapping area vessel pixels with the part of the second overlapping area vessel pixels, compare a first peripheral image with a second peripheral image, wherein the first peripheral image is an image of an area including first unassociated pixels in the first overlapping area vessel pixels, which are not associated with the second overlapping area vessel pixels, the second peripheral image is an image of an area including second unassociated pixels corresponding to the first peripheral image in the time-series images, and when degree of coincidence between the first peripheral image and the second peripheral image exceeds a specified value, associate the first unassociated pixels with the second unassociated pixels to associate the vessel pixel in the overlapping area in the one of the time-series images with the vessel pixel in the overlapping area in the other as having the correspondence relationship.

6. The medical image analyzer of claim 3, wherein the processing circuitry is further configured to select pixels representing a branch point of a blood vessel from among the pixels of the time-series images as the vessel pixels, and select a pixel representing a branch point of a blood vessel from among the pixels of the entire area image as the entire area vessel pixel.

7. The medical image analyzer of claim 2, wherein the processing circuitry is further configured to store, in advance, blood vessel classification information that represents characteristics of each type of blood vessel, determine type of the blood vessel represented by the vessel pixels associated based on the blood vessel transition information and the blood vessel classification information, and include the type of the blood vessel determined in the blood vessel transition information to obtain the second artery transition information.

8. The medical image analyzer of claim 1, wherein the processing circuitry is further configured to select pixels representing a branch point of a blood vessel from among the pixels of the time-series images as the vessel pixels.

9. The medical image analyzer of claim 1, wherein the processing circuitry is further configured to obtain, with respect to each of the time-series images, artery residue information that represents a transition of pixel value due to the contrast agent administered for capturing a previous time-series image based on either or both of the first artery transition information and the second artery transition information, obtain tissue transition information that represents a transition of pixel value of each pixel in the time-series images, obtain tissue residue information that represents a transition of pixel value based on the artery residue information with respect to each pixel of the time-series images, and subtract the pixel value represented by the tissue residue information from the pixel value represented by the tissue transition information.

10. A medical image analyzer configured to analyze time-series images of a subject to obtain hemodynamics of the subject, the medical image analyzer comprising processing circuitry configured to:

retrieve a plurality of time-series images captured of a plurality of areas of a subject having been administered a contrast agent at different times;

obtain first artery transition information that represents a transition of pixel value in an artery area based on the artery area specified in a part of the time-series images;

perform registration between pixels in frames of the time-series image to obtain results of the registration as time-phase association information;

extract an image area that represents tissue to be analyzed from each of the time-series images;

receive the time-series images, the time-phase association information and the image area, extract artery pixels from the image area, and obtain artery pixel transition information that represents a transition of pixel value of each the artery pixels, and obtain transition information of the artery area over capturing time of all the time-series images as second artery transition information based on time information indicating a time of capturing each of the time-series images, the artery pixel transition information, and the first artery transition information.

11. The medical image analyzer of claim 10, wherein the processing circuitry is further configured to obtain, with respect to each of the time-series images, artery residue information that represents a transition of pixel value due to the contrast agent administered for capturing a previous time-series image based on either or both of the first artery transition information and the second artery transition information, obtain tissue transition information that represents a transition of pixel value of each pixel in the time-series images, obtain tissue residue information that represents a transition of pixel value based on the artery residue information with respect to each pixel of the time-series images, and subtract the pixel value represented by the tissue residue information from the pixel value represented by the tissue transition information.

12. The medical image analyzer of claim 11, wherein the processing circuitry is further configured to perform model fitting using an imaging model specified by either or both of the first artery transition information and the second artery transition information, the artery residue information, and the tissue transition information to obtain a parameter related to the imaging model, and obtain the tissue residue information based on the artery residue information, the imaging model, and the parameter obtained.

13. The medical image analyzer of claim 12, wherein the processing circuitry is further configured to obtain, as the parameter, a damping time constant representing attenuation of the pixel value of each pixel in the time-series images.

* * * * *